United States Patent
Nakazato et al.

(10) Patent No.: US 6,333,358 B1
(45) Date of Patent: Dec. 25, 2001

(54) ARYLOXYANILINE DERIVATIVES

(75) Inventors: Atsuro Nakazato; Taketoshi Okubo; Toshio Nakamura; Shigeyuki Chaki; Kazuyuki Tomisawa, all of Tokyo; Masashi Nagamine, Osaka; Kenji Yamamoto, Osaka; Koichiro Harada, Osaka; Masanori Yoshida, Osaka, all of (JP)

(73) Assignees: Taisho Pharmaceutical Co., Ltd.; Nihon Nohyaku Co., Ltd., both of (JP)

( * ) Notice: Subject to any disclaimer, the term of this patent is extended or adjusted under 35 U.S.C. 154(b) by 0 days.

(21) Appl. No.: 09/485,006

(22) PCT Filed: Aug. 3, 1998

(86) PCT No.: PCT/JP98/03442

§ 371 Date: Feb. 1, 2000

§ 102(e) Date: Feb. 1, 2000

(87) PCT Pub. No.: WO99/06353

PCT Pub. Date: Feb. 11, 1999

(30) Foreign Application Priority Data

Aug. 4, 1997 (JP) ................................... 9-209123

(51) Int. Cl.$^7$ ....................... A61K 31/135; A61K 31/165
(52) U.S. Cl. ............................... 514/650; 514/651
(58) Field of Search ..................... 514/650, 651

(56) References Cited

U.S. PATENT DOCUMENTS 6,071,920 * 6/2000 Leonardi et al. ................. 514/255

FOREIGN PATENT DOCUMENTS

| 826673 | 10/1996 | (EP) . |
| 57-208295 | 12/1982 | (JP) . |
| 61-40249 | 2/1986 | (JP) . |
| 61040249 | * 2/1986 | (JP) . |
| 95/33715 | 12/1995 | (WO) . |

OTHER PUBLICATIONS

Ashton, P.R., et al, Synthesis of Ligands Containing Two and Three 2,2'–(Bisamino)diphenyl Ether Units Designed for Molecular Self–Assembly on Lithiation, Synthesis, Aug. 1996, No. 8, pp. 930–930, Particularly refer to p. 934.

* cited by examiner

Primary Examiner—Mukund J. Shah
Assistant Examiner—Sudhaker B. Patel
(74) Attorney, Agent, or Firm—Lorusso & Loud

(57) ABSTRACT

An aryloxyaniline derivative represented by the formula:

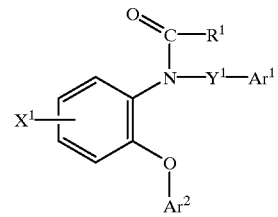

wherein $Ar^1$ and $Ar^2$ are each a substituted or unsubstituted phenyl group, pyridyl group or naphthyl group, $R^1$ is a hydrogen atom, an alkyl group, etc., $X^1$ is a hydrogen atom, an alkyl group, etc., $y^1$ is a branched or unbranched alkylene group having 1 to 6 carbon atoms or a single bond; or a pharmaceutically acceptable salt thereof can provide medicines having a high affinity for MDR, and therefore, exhibiting a therapeutic or preventive effect on anxiety, related diseases thereto, depression, etc.

3 Claims, No Drawings

ARYLOXYANILINE DERIVATIVES

TECHNICAL FIELD

The present invention relates to a medicine, and more particularly relates to a medicine having a high affinity for MDR.

BACKGROUND ART

Benzodiazepine (Bz) receptors are recently classified into 2 subtypes of central benzodiazepine receptor (CBR) located on $GABA_A$ receptor/ion channel complex and mitochondrial DBI (diazepam binding inhibitor, Neuropharmacol., 30, 1425–1433 (1991)) receptor (BDR) located on the central nervous system (glial cells) or adrenal glands (Clin. Neuropharmacol., 16, 401–417 (1993)).

MDR agonists act indirectly on $GABA_A$/ion channel complex via endogenous neurosteroids and cause an anti-anxiety action. Accordingly, they have a possibility to be usable for diseases (obsessive disorders, panic disorders) on which the previous Bzs do not have a satisfactorily therapeutic effect, and to alleviate side-effects such as excessive sedation or psychic dependence caused by the Bzs. Furthermore, MDR ligands act indirectly on $GABA_A$ receptors, and therefore, have a possibility of use as therapeutical agents of sleeping disorders, epilepsy, dyskinesia accompanied by muscle rigidity, feeding disorders, circulation disorders, recognition and learning disability or drug dependence (Progress in Neurobiology, 38, 379–395, 1992, ibid., 49, 73–97, 1996; J. Neurochem., 58, 1589–1601; Neuropharmacol., 30, 1435–1440, 1991). In addition, MDR ligands have a possibility of use as therapeutic agents of cancer (Biochimica et Biophysica Acta, 1241, 453–470, 1995), lipid metabolism abnormality (Eur. J. Pharmacol., 294, 601–607, 1995), schizophrenia (Neuropharmacology, 35, 1075–1079, 1996), cerebral infarction (J. Neurosci., 15, 5263–5274, 1995), AIDS (Abstracts of the fifth international conference on AIDS, p. 458, 1989), Alzheimer's disease (Alzheimer Dis. Assoc. Disotd., 2, 331–336, 1988) or Huntington chorea (Brain Res., 248, 396–401, 1982).

Some phenoxyaniline derivatives are reported in WO9533715, JP 61040249 and JP 57208295. However, they have a hydrogen atom or an alkyl group as the substituent on the nitrogen atom of the aniline, but there are not reported the derivatives having a carbonyl group as the substituent. Furthermore, the use of the derivatives of the above-mentioned patent is anti-inflammatory agents based on the action to arakidonic acid series, anti-arteriosclerosis drugs based on an increase of $PGI_2$ production, or heat sensitive recording materials, but there is not described affinity for MDR and anti-anxiety based on affinity for MDR.

An object of the present invention is to provide pharmaceutical compounds which are effective on diseases on which the previous Bzs do not have a satisfactorily therapeutic effect, and have a high affinity for MDR, and therefore, have a therapeutic or preventive effect on the central diseases such as anxiety, related diseases thereto, depression, epilepsy, etc. without side-effects such as excessive sedation or psychic dependence caused by the Bzs. Furthermore, another object of the present invention is to provide therapeutic agents of sleeping disorders, dyskinesia accompanied by muscle rigidity, feeding disorders, circulation disorders, recognition and learning disability, drug dependence, cancer, lipid metabolism abnormality, schizophrenia, cerebral infarction, AIDS, Alzheimer's disease or Huntington chorea.

DISCLOSURE OF THE INVENTION

As a result of extensive researches about aryloxyaniline derivatives, the present inventors have found novel aryloxyaniline derivatives having a high affinity for MDR, thus the present invention has been accomplished.

The present invention is illustrated as follows: the present invention is directed to an aryloxyaniline derivative represented by Formula [I]:

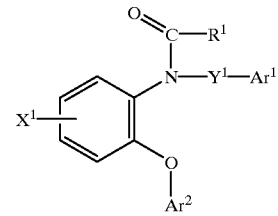

wherein $Ar^1$ and $Ar^2$ are the same or different, and are each a substituted or unsubstituted phenyl group, a substituted or unsubstituted pyridyl group or naphthyl group, $R^1$ is a hydrogen atom, a substituted or unsubstituted alkyl group having 1 to 10 carbon atoms, an alkoxy group having 1 to 10 carbon atoms, a substituted or unsubstituted phenyl group or group of the formula:

—$NR^2(R^3)$ (wherein $R^2$ and $R^3$ are the same or different, and are each a hydrogen atom or an alkyl group having 1 to 10 carbon atoms, or $R^2$ and $R^3$ taken together with the nitrogen atom to which they are attached form a 4 to 10 membered cyclic amino group), $X^1$ is a hydrogen atom, an alkyl group having 1 to 5 carbon atoms, an alkoxy group having 1 to 5 carbon atoms, a phenoxy group, a halogen atom, a trifluoro methyl group, a carbamoyl group or an aminosulfonyl group, $y^1$ is a branched or unbranched alkylene group having 1 to 6 carbon atoms or a single bond; or a pharmaceutically acceptable salt thereof.

In the present invention, the substituted phenyl group is a phenyl group substituted with one to three members selected from the group consisting of an alkyl group having 1 to 10 carbon atoms, an alkyl group having 1 to 10 carbon atoms substituted with halogen atoms; hydroxyl groups; alkanoyloxy groups having 1 to 10 carbon atoms; carboxyl groups or alkoxycarbonyl groups, an alkenyl group having 2 to 10 carbon atoms, an alkoxy group having 1 to 10 carbon atoms, an alkylthio group having 1 to 10 carbon atoms, a group of the formula: —O—Z—$R^4$ (wherein Z is a branched or unbranched alkylene group having 1 to 10 carbon atoms, and $R^4$ is an amino group, an amino group substituted with one or two of an alkyl group having 1 to 7 carbon atoms, a cyclic amino group having 2 to 7 carbon atoms, a hydroxyl group, a carboxyl group or an alkoxycarbonyl group), an alkanoyl group having 2 to 10 carbon atoms or a ketal form thereof, a formyl group or an acetal form thereof, a carboxyl group, an alkoxycarbonyl group having 2 to 10 carbon atoms, a carbamoyl group, a carbamoyl group substituted with one or two of an alkyl group having 1 to 10 carbon atoms on the nitrogen atom, an aminosulfonyl group, an aminosulfonyl group substituted with one or two of an alkyl group having 1 to 10 carbon atoms on the nitrogen atom, a halogen atom and a nitro group, and examples thereof are a 2-methylphenyl group, a 2-propylphenyl group, a 2-isopropylphenyl group, a 2-cyclopentylphenyl group, a 2-(1-hydroxyethyl)phenyl group, a 2-carboxymethylphenyl group, a 2-methoxycarbonyl phenyl group, a 2-vinylphenyl group, a 2-methoxyphenyl group, a 3-methoxyphenyl group, a 4-methoxyphenyl group, a 2-ethoxyphenyl group, a 2-hexyloxyphenyl group, a 2-isopropoxyphenyl group, a 2-cyclopentoxyphenyl group, a 2,5-dimethoxyphenyl group, a 2,4,6-trimethoxyphenyl group, a 4-methylthiophenyl group, a 2-isopropylthiophenyl group, a 4-cyclohexylthiophenyl group, a 2-(2-dimethylamino ethoxy)phenyl group, a 2-(2-hydroxyethoxy)phenyl group, a 2-carboxymethoxyphenyl group, a 2-methoxycarbonylmethoxyphenyl group, a 2-acetylphenyl group, a 2-(2-methyl-1,3-dioxolan-2-yl)phenyl group, a 2-formylphenyl group, a 2-(1,3-dioxolan-2-yl)phenyl group, a 2-carboxylphenyl group, a 2-(N-methylaminocarbonyl) phenyl group, a 2-(N,N-dimethylamino-carbonyl)phenyl group, a 2-aminocarbonylphenyl group, a 2-aminosulfonylphenyl group, a 4-aminosulfonylphenyl group, a 2-methylaminosulfonylphenyl group, a 2-dimethylamino-sulfonylphenyl group, a 2-fluorophenyl group, a 3-fluorophenyl group, a 4-fluorophenyl group, a 2-chlorophenyl group, a 3-chlorophenyl group, a 4-chlorophenyl group, a 2-bromophenyl group, a 3-bromophenyl group, a 4-bromophenyl group, a 2,4-difluorophenyl group, a 2-nitrophenyl group, a 2-aminophenyl group, a 2-pyrrolidinophenyl group and a 4-dimethylaminophenyl group. The substituted pyridyl group refers to a pyridyl group substituted with a straight or branched alkoxy group having 1 to 10 carbon atoms, and examples thereof are a 2-methoxy-3-pyridyl group, a 3-methoxy-2-pyridyl group and a 4-methoxy-3-pyridyl group. The alkyl group having 1 to 10 carbon atoms refers to a straight, branched or cyclic alkyl group, and examples thereof are a methyl group, an ethyl group, a propyl group, an isopropyl group, a cyclopropyl group, a butyl group, an isobutyl group, a cyclobutyl group, a cyclopropylmethyl group, a pentyl group, an isopentyl group, a cyclopentyl group, a cyclobutylmethyl group, a 1-ethylpropyl group, a hexyl group, an isohexyl group, a cyclohexyl group, a cyclopentylmethyl group, a 1-ethylbutyl group, a heptyl group, an isoheptyl group, a cyclohexylmethyl group, an octyl group, a nonyl group and a decyl group. The substituted alkyl group having 1 to 10 carbon atoms refers to an alkyl group substituted with a hydroxyl group, an alkanoyloxy group, an alkanoyl group, an alkoxy group, a halogen atom, an azido group, an amino group or a carboxyl group, and examples thereof are a hydroxymethyl group, an acetyloxymethyl group, a methoxymethyl group, a chloromethyl group, a trifluoromethyl group, an azidomethyl group, an aminomethyl group, a dimethylaminomethyl group and a pyrrolidinomethyl group. The alkoxy group having 1 to 10 carbon atoms refers to a straight, branched or cyclic alkoxy group, and examples thereof are a methoxy group, an ethoxy group, a propoxy group, an isopropoxy group, a butoxy group, an isobutoxy group, a cyclopropylmethoxy group, a pentyloxy group, an isopentyloxy group, a hexyloxy group, a heptyloxy group, an octyloxy group, a nonyloxy group and a decyloxy group. The alkyl group having 1 to 10 carbon atoms represented by $R^2$ and $R^3$ refers to a straight, branched or cyclic alkyl group, accordingly, when $R^2$ and $R^3$ are each the alkyl group having 1 to 10 carbon atoms, examples of the group of $—NR^2(R^3)$ are a methylamino group, an ethylamino group, a propylamino group, an isopropylamino group, a butylamino group, an isobutylamino group, a cyclopropylmethylamino group, a pentylamino group, an isopentylamino group, a cyclopentylamino group, a cyclobutylmethylamino group, a 1-ethylpropylamino group, a hexylamino group, an isohexylamino group, a cyclohexylamino group, a cyclopentyl methylamino group, a 1-ethylbutylamino group, a heptylamino group, an isoheptylamino group, a cyclohexylmethylamino group, an octylamino group, a nonylamino group, a decylamino group, a dimethylamino group, a diethylamino group, a dipropylamino group, a dibutylamino group, a dipentylamino group, a dihexylamino group, an N-methylethylamino group, an N-methylpropylamino group, an N-methylbutylamino group, an N-methylpentylamino group, an N-methylhexylamino group, an N-ethylpropylamino group, an N-ethylbutylamino group and an N-ethylpentylamino group. The 4 to 10 membered cyclic amino group represented by the group of $—NR^2(R^3)$ refers to a cyclic amino group which may optionally have a nitrogen atom or an oxygen atom, and examples thereof are a pyrrolidino group, a piperidino group, a piperazino group, an N-methylpiperazino group and a morpholino group. The alkyl group having 1 to 5 carbon atoms represented by $X^1$ refers to a straight, branched or cyclic alkyl group, and examples thereof are a methyl group, an ethyl group, a propyl group, an isopropyl group, a cyclopropyl group, a butyl group, an isobutyl group, a cyclobutyl group and a cyclopropylmethyl group. The alkoxy group having 1 to 5 carbon atoms refers to a straight, branched or cyclic alkoxy group, and examples thereof are a methoxy group, an ethoxy group, a propoxy group, an isopropoxy group, a butoxy group, an isobutoxy group and a cyclopropylmethoxy group. Examples of the branched or unbranched alkylene group having 1 to 6 carbon atoms represented by $Y^1$ are a methylene group, an ethylene group, a propylene group, a methylmethylene group and a dimethylmethylene group. The halogen atom refers to a fluorine atom, a chlorine atom, a bromine atom or an iodine atom.

Examples of the pharmaceutically acceptable salt in the present invention are salts with mineral acids (e.g. sulfuric acid, hydrochloric acid or phosphoric acid), organic acids (e.g. acetic acid, oxalic acid, lactic acid, tartaric acid, fumaric acid, maleic acid, methanesulfonic acid or benzenesulfonic acid), metal ions (e.g. a sodium ion, a potassium ion or a calcium ion), organic bases (e.g. diethanolamine) or ammonium salt.

The compound of Formula [I] can be prepared by the following general preparation methods 1 to 6. In the following reaction formulae, $Ar^1$, $Ar^2$, $R^1$, $X^1$ and $Y^1$ are as defined above, $Y^2$ is a single bond or an allcylene group having 1 to 5 carbon atoms which is unsubstituted or substituted with an alkcyl group having 1 to 3 carbon atoms, $R^5$ is an alkyl group having 1 to 3 carbon atoms or a hydrogen atom, $X^2$ is an acyloxy group having 1 to 10 carbon atoms, a chlorine atom, a bromine atom, a hydroxyl group or an alkoxy group having 1 to 5 carbon atoms, $X^3$ is a chlorine atom, a bromine atom or an iodine atom.

GENERAL PREPARATION METHOD 1

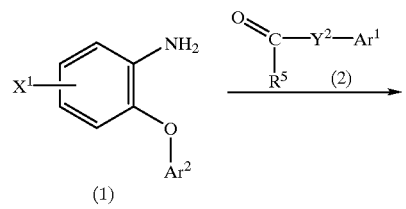

-continued

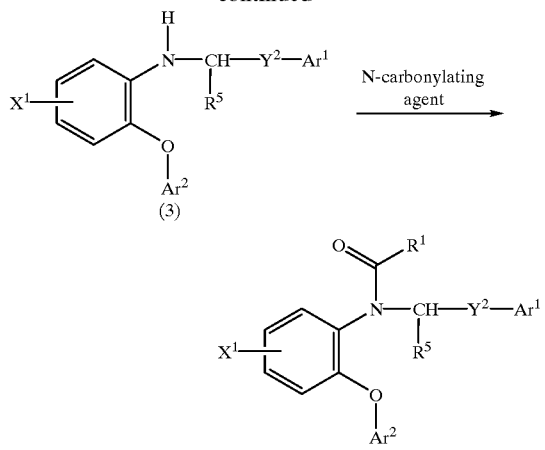

An aniline derivative (1) is reacted with a carbonyl derivative (2) in the presence or absence of an acid catalyst in an inert solvent and subjected to reduction, or a mixture of the aniline derivative (1) and the carbonyl derivative (2) is subjected to reduction in the presence or absence of an acid catalyst in an inert solvent to give a compound (3). The compound (3) is reacted with an N-carbonylating agent in the presence or absence of a base in an inert solvent to give a compound (4) of the present invention. Alternatively, phosgene as the N-carbonylating agent is reacted with the compound (3) to give a chlorocarbonyl derivative, which is then reacted with an alcohol or an amine in the presence or absence of a base, thereby the compound (4) of the present invention is also obtained.

Examples of the acid catalyst are a halogenated hydrogen (e.g. hydrogen chloride or hydrogen bromide), an inorganic acid (e.g. hydrochloric acid or sulfuric acid), an organic acid (e.g. acetic acid or tosylic acid), PPTS, piperidine hydrochloride, etc.

The reduction is carried out by using a borane reductant (e.g. sodium borohydride, lithium borohydride or sodium cyanoborohydride), or an aluminum reductant (e.g. lithium-aluminum hydride), or carried out by hydrogenation using a catalyst such as palladium, platinum dioxide or Raney nickel. Examples of the N-carbonylating agent are an acyl halide, an organic acid anhydride, an alkoxycarbonyl halide, a carbamoyl halide, cyanic acid (formed from potassium cyanate and acetic acid in the reaction solution) and an isocyanate. Examples of the base are an organic amine (e.g. triethylamine, diisopropylethylamine or pyridine), and an inorganic base (e.g. potassium carbonate, sodium hydroxide, sodium hydride or a metallic sodium). Examples of the inert solvent are an alcohol (e.g. methanol or ethanol), an ether (e.g. tetrahydrofuran), a hydrocarbon (e.g. toluene or benzene), a halogenated hydrocarbon solvent (e.g. chloroform or dichloromethane), acetonitrile, water and a mixture thereof.

GENERAL PREPARATION METHOD 2

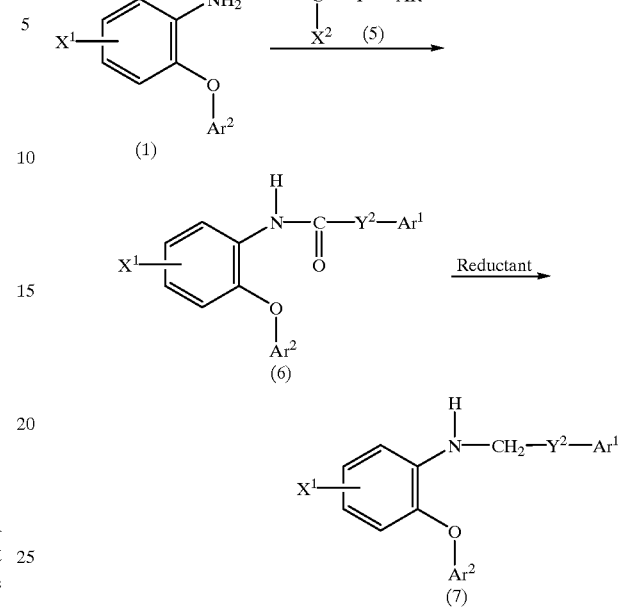

A compound (7), i.e. the compound (3) wherein $R^5$ is a hydrogen atom, is also obtained by reacting the aniline derivative (1) with a carboxylic anhydride, an acyl halide, a carboxylic acid or a carboxylic acid ester, each of which is represented by a compound (5), in the presence or absence of a base in an inert solvent to give an amide compound (6), and then reacting the amide compound (6) with a reductant in an inert solvent.

GENERAL PREPARATION METHOD 3

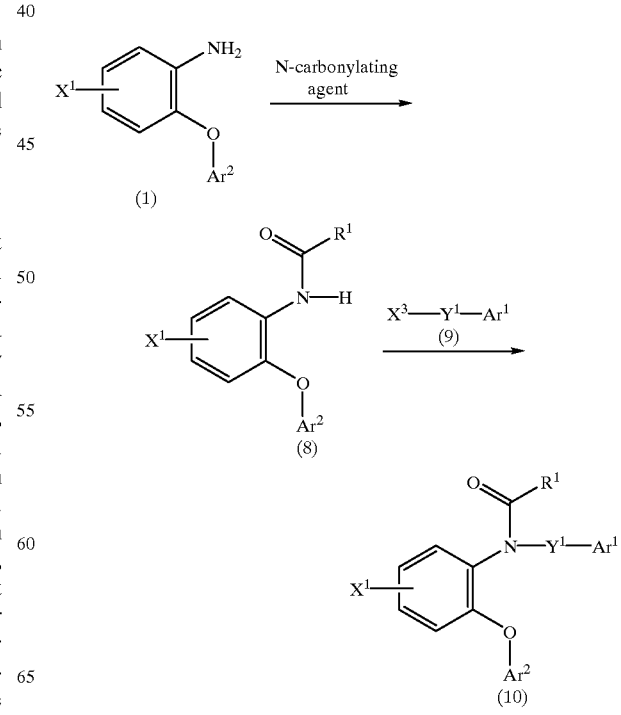

The aniline derivative (1) is reacted with an N-carbonylating agent in the presence or absence of a base in an inert solvent to give a compound (8), which is then reacted with a halogenated compound (9) in the presence of a base, if necessary, by using a phase transfer catalyst, a copper powder or a cuprous halide in an inert solvent, thereby there is obtained a compound (10) of the present invention. Alternatively, phosgene as the N-carbonylating agent is reacted with the compound (1) to give a chlorocarbonyl derivative, which is then reacted with an alcohol or an amine in the presence of a base, thereby there is also obtained the compound (8).

Examples of the N-carbonylating agent are an acyl halide, an organic acid anhydride, an allcoxycarbonyl halide, a carbamoyl halide, cyanic acid (formed from potassium cyanate and acetic acid in the reaction solution) and an isocyanate. Examples of the base are an organic amine (e.g. triethylamine, diisopropylethylamine or pyridine), an inorganic base (e.g. potassium carbonate, sodium hydroxide, sodium hydride or metallic sodium) and an alcoholate (e.g. potassium t-butoxide or sodium ethoxide). Examples of the phase transfer catalyst are a quaternary ammonium salt (e.g. benzyltriethyl ammonium bromide) or a crown ether (e.g. 18-crown-6 ether). Examples of the inert solvent are an alcohol (e.g. methanol or ethanol), an ether (e.g. tetrahydrofuran), a hydrocarbon (e.g. toluene or benzene), a halogenated hydrocarbon solvent (e.g. dichloromethane or chloroform), a ketone solvent (e.g. acetone), acetonitrile, N,N-dimethylformamide, nitrobenzene, water and a mixture thereof.

GENERAL PREPAATION METHOD 4

When one or both of $Ar^1$ and $Ar^2$ have nitro groups, the nitro groups can be each converted into an amino group by a hydrogenation or a metal reduction. The amino group is reacted with a halogenated compound in the presence of a base, if necessary, by using a phase transfer catalyst in an inert solvent to be converted into an amino group substituted with a straight, branched or cyclic alkyl group having 1 to 10 carbon atoms.

The hydrogenation is carried out by using a catalyst such as palladium, platinum dioxide or Raney nickel, and the metal reduction is carried out by using a metal or a metal salt such as tin, a stannous salt (e.g. stannous chloride), iron, a ferrous salt (e.g. ferrous chloride) or zinc under conventional acidic, basic or neutral conditions. Examples of the base are an organic amine (e.g. triethylamine, diisopropylethylamine or pyridine), an inorganic base (e.g. potassium carbonate, sodium hydroxide, sodium hydride or metallic sodium), and an alcoholate (e.g. potassium t-butoxide or sodium ethoxide). Examples of the phase transfer catalyst are a quaternary ammonium salt (e.g. benzyltriethyl ammonium bromide) and a crown ether (e.g. 18-crown-6 ether). Examples of the inert solvent are an alcohol (e.g. methanol or ethanol), an ether (e.g. tetrahydrofuran), a hydrocarbon (e.g. toluene or benzene), a halogenated hydrocarbon solvent (e.g. dichloromethane or chloroform), acetonitrile, N,N-dimethylformamide, water and a mixture thereof.

GENERAL PREPARATION METHOD 5

When one or both of $Ar^1$ and $Ar^2$ have acyloxy groups, the acyloxy groups can be each converted into a hydroxyl group by hydrolysis under acidic or basic conditions. The hydroxyl group is reacted with a halogenated compound in the presence of a base, if necessary, by using a phase transfer catalyst in an inert solvent to be converted into a straight or branched alkoxy group having 1 to 10 carbon atoms, a straight or branched alkoxy group having 1 to 10 carbon atoms which is substituted with a substituted or unsubstituted amino group, or an alkoxy group having 1 to 10 carbon atoms which is substituted with a carboxyl group or an alkoxycarbonyl group.

The acidic or basic conditions mean to use an inorganic acid (e.g. hydrochloric acid or sulfuric acid) or an inorganic base (e.g. sodium hydroxide or potassium hydroxide) in a solvent such as an alcohol (e.g. methanol or ethanol), an ether (e.g. tetrahydrofuran or dioxane), a ketone (e.g. acetone), acetonitrile, N,N-dimethylformamide, water or a mixture thereof. Examples of the base are an organic amine (e.g. triethylamine, diisopropylethylamine or pyridine), an inorganic base (e.g. potassium carbonate, sodium hydroxide, sodium hydride or metallic sodium), and an alcoholate (e.g. potassium t-butoxide or sodium ethoxide). Examples of the phase transfer catalyst are a quaternary ammonium salt (e.g. benzyltriethyl ammonium bromide) and a crown ether (e.g. 18-crown-6 ether). Examples of the inert solvent are an alcohol (e.g. methanol or ethanol), an ether (e.g. tetrahydrofuran), a hydrocarbon (e.g. toluene or benzene), a halogenated hydrocarbon solvent (e.g. dichloromethane or chloroform), acetonitrile, N,N-dimethylformamide, water and a mixture thereof.

GENERAL PREPARATION METHOD 6

When one or both of $Ar^1$ and $Ar^2$ have alkoxycarbonyl groups, the alkoxycarbonyl groups are each converted under conventional hydrolysis conditions of an ester into a carboxyl group, which can be then converted into an alkoxycarbonyl group having 1 to 10 carbon atoms by esterification, or into a primary or secondary alkylaminocarbonyl group having 1 to 10 carbon atoms or an aminocarbonyl group by amidation.

The hydrolysis conditions mean a reaction of a base (e.g. sodium hydroxide or potassium hydroxide or sodium carbonate) or an inorganic acid (e.g. hydrochloric acid or sulfuric acid) in an inert solvent such as an alcohol (e.g. methanol or ethanol) or a ketone (e.g. acetone). The esterification means a reaction of an alkyl compound which is substituted with chlorine atoms, bromine atoms or iodine atoms, or a dialkyl sulfate, together with an inorganic base (e.g. sodium hydroxide, potassium hydroxide, sodium carbonate, potassium carbonate or sodium hydride), an alcoholate (e.g. sodium methoxide or potassium t-butoxide) or an organic base (e.g. triethylamine or diisopropylethylamine), or a reaction of an alcohol with an acid (e.g. hydrogen chloride or sulfuric acid). The amidation is carried out by converting the carboxyl group with thionyl chloride or triphenylphosphine-carbon tetrachloride into an acid halide, and then by reacting the acid halide with a corresponding amine derivative, or carried out by a conventional amidation (e.g. a mixed acid anhydride method or a dicyclohexylcarbodiimide method).

GENERAL PREPARATION METHOD 7

When one or both of $Ar^1$ and $Ar^2$ have formyl or acyl groups, carbonyl groups of the formyl or acyl groups are each reacted with a Wittig reagent to be converted into an alkenyl group, which is then converted into an alkyl group by reduction.

The Wittig reagent includes a triphenylalkyl phosphonium halide having an alkyl group having 1 to 9 carbon atoms or a diethylalkyl phosphonate, and it is used in an inert solvent such as an alcohol (e.g. methanol or ethanol), an ether (e.g. tetrahydrofuran), a hydrocarbon (e.g. toluene or benzene), a halogenated hydrocarbon (e.g. methylene chloride or chloroform), acetonitrile or N,N-dimethylformamide together with a base such as sodium hydride, potassium t-butoxide, sodium ethoxide or n-butyl lithium, if necessary, further together with a phase transfer catalyst such as a quaternary ammonium salt (e.g. benzyltriethyl ammonium bromide) or a crown ether (e.g. 18-crown-6 ether). The reduction includes hydrogenation which is carried out by using a catalyst such as palladium, platinum dioxide or Raney nickel.

GENERAL PREPARATION METHOD 8

When one or both of $Ar^1$ and $Ar^2$ have formyl or acyl groups, carbonyl groups of the formyl or acyl groups are each reacted with a Grignard reagent to be converted into a sec- or tert-alcohol compound. The sec-alcohol compound is oxidized with various oxidants to be converted into an acyl group.

The Grignard reagent includes an alkyl or alkenyl magnesium halide having 1 to 9 carbon atoms such as methyl magnesium bromide or ethyl magnesium bromide. The oxidant includes oxalyl chloride-dimethyl sulfoxide (Swern Oxidation), a chromic oxidant, a metal oxidant such as manganese dioxide.

For the use of the compounds of the present invention as medicines, the compounds of the present invention are mixed with conventional additives such as a filler, a binder, a disintegrater, a pH regulator or a solubulizer to form tablets, pills, capsules, granules, powders, solutions, emulsions, suspensions or injections, all of which can be prepared by conventional techniques.

The compound of the present invention can be administered orally or parenterally in the amount of from 0.1 to 500 mg/day to an adult patient in a single dose or several divided doses. This dose can be varied depending on the type of diseases, age, body weight or symptoms of each patient.

BEST MODE OF CARRYING OUT THE INVENTION

The present invention is illustrated in more detail by showing the following examples and experiments.

EXAMPLE 1

Synthesis of N-acetyl-N-(2-isopropoxybenzyl)-2-phenoxyaniline (1) To a solution of 1.64 g of 2-isopropoxybenzaldehyde in 10 ml of methanol was added 1.85 g of 2-aminodiphenyl ether, and then the mixture was stirred at room temperature for 30 minutes and cooled on ice-water. To the cooled reaction solution was gradually added 1.50 g of sodium borohydride, followed by stirring under ice-cooling for 30 minutes and then at room temperature for 30 minutes. An aqueous acetic acid solution (1.5 ml of acetic acid-30 ml of water) was added dropwise to the reaction solution, followed by stirring at room temperature for 10 minutes. After extraction with ethyl acetate, the extract was washed with a saturated aqueous sodium bicarbonate solution and a saturated aqueous sodium chloride solution and dried over anhydrous sodium sulfate. After removal of the drying agent by filtration, the filtrate was concentrated under reduced pressure, and the residue was purified by silica gel column chromatography (eluent; ethyl acetate-hexane=1:25) to give 2.65 g of N-(2-isopropoxybenzyl)-2-phenoxyaniline as an oil.

(2) In 30 ml of tetrahydrofuran were dissolved 2.65 g of N-(2-isopropoxybenzyl)-2-phenoxyaniline and 1.5 ml of triethylamine, and then 0.8 ml of acetyl chloride was added dropwise to the solution with stirring, followed by stirring for 30 minutes. The reaction mixture was poured to water and extracted with ethyl acetate, and the extract was washed with 0.5 N hydrochloric acid, a saturated aqueous sodium bicarbonate solution and then with a saturated aqueous sodium chloride solution, successively, and dried over anhydrous sodium sulfate. After removal of the drying agent by filtration, the filtrate was concentrated under reduced pressure, and the residue was purified by silica gel column chromatography (eluent; ethyl acetate-hexane=1:4) to give 2.92 g of N-acetyl-N-(2-isopropoxybenzyl)-2-phenoxyaniline as an oil.

The structures and physical property data of the present compound and the compounds prepared similarly are shown in Tables 1 and 2.

EXAMPLE 2

Synthesis of N-acetyl-N-(2,4-dimethoxybenzyl)-2-phenoxyaniline (1) In 60 ml of methanol were dissolved 3.70 g of 2-aminodiphenyl ether and 3.70 g of 2,4-dimethoxybenzaldehyde, and then 70 mg of platinum oxide was added, followed by stirring at room temperature under a hydrogen stream overnight. To the reaction mixture was added 30 ml of chloroform for dissolving the precipitate, and the catalyst was separated by filtration. The filtrate was concentrated under reduced pressure, and the residue was recrystallized from methanol to give 5.06 g of N-(2,4-dimethoxybenzyl)-2-phenoxyaniline.

(2) To a solution of 1.00 g of N-(2,4-dimethoxy benzyl)-2-phenoxyaniline in 1.18 g of pyridine was added 0.76 g of acetic anhydride, followed by stirring at room temperature for a day. The reaction mixture was poured into water and extracted with ethyl acetate, and the extract was washed with 0.5 N hydrochloric acid, a saturated aqueous sodium bicarbonate solution and a saturated aqueous sodium chloride solution, successively, and dried over anhydrous sodium sulfate. After removal of the drying agent by filtration, the solvent was concentrated under reduced pressure, and the residue was purified by silica gel column chromatography (eluent; ethyl acetate-hexane=1:3) to give 1.09 g of N-acetyl-N-(2,4-dimethoxybenzyl)-2-phenoxyaniline as an oil.

The structures and physical property data of the present compound and the compounds prepared similarly are shown in Tables 1 and 2.

EXAMPLE 3

Synthesis of N-acetyl-N-(2-chlorobenzyl)-2-phenoxyaniline (1) To a solution of 28.5 g of 2-phenoxyaniline and 25.8 ml of triethylamine in 250 ml of methylene chloride was added dropwise 11.5 ml of acetyl chloride under ice-cooling. After stirring at room temperature for 1.5 hours, the reaction mixture was concentrated under reduced pressure, and the residue was poured into water and extracted with ethyl acetate. The extract was washed with 0.5 N hydrochloric acid, a saturated aqueous sodium bicarbonate solution and a saturated aqueous sodium chloride solution, successively, and dried over anhydrous sodium sulfate. After removal of the drying agent by filtration, the solvent was concentrated under reduced pressure, and the residue was purified by silica gel column chromatography (eluent; ethyl acetate-hexane=1:4) to give 33.7 g of N-acetyl-2-phenoxyaniline.

(2) To a suspension of 400 mg of sodium hydride (60% in oil) in 30 ml of dimethylformamide was added 2.00 g of N-acetyl-2-phenoxyaniline at room temperature, followed by stirring at room temperature for 30 minutes. To the solution was added dropwise 1.64 g of 2-chlorobenzyl chloride at room temperature with stirring, followed by stirring for 30 minutes. After addition of ice-water, the reaction mixture was extracted with ether. The extract was washed with 0.5 N hydrochloric acid, a saturated aqueous sodium bicarbonate solution and a saturated aqueous sodium chloride solution, successively, and dried over anhydrous sodium sulfate. After removal of the drying agent by filtration, the solvent was concentrated under reduced pressure, and the residue was purified by silica gel column chromatography (eluent; ethyl acetate-hexane=1:4) to give 2.92 g of N-acetyl-N-(2-chlorobenzyl)-2-phenoxyaniline as an oil.

The structures and physical property data of the present compound and the compounds prepared similarly are shown in Tables 1 and 2.

EXAMPLE 4
Synthesis of N-aminocarbonyl-N-(2-methoxybenzyl)-2-phenoxyaniline

In 20 ml of acetic acid was dissolved 1.54 g of N-(2-methoxybenzyl)-2-phenoxyaniline synthesized in the same manner as in Example 1(1), and then an aqueous potassium cyanate solution (1.23 g of potassium cyanate and 10 ml of water) was added dropwise to the solution, followed by stirring at room temperature for 2.5 hours. The reaction mixture was poured into water and extracted with ethyl acetate, and the extract was washed with a saturated aqueous sodium bicarbonate solution and a saturated sodium chloride solution and dried over anhydrous sodium sulfate. After removal of the drying agent by filtration, the solvent was concentrated under reduced pressure, and the residue was purified by silica gel column chromatography (eluent; ethyl acetate-hexane=1:3) to give 1.69 g of N-aminocarbonyl-N-(2-methoxybenzyl)-2-phenoxyaniline as an oil.

The structures and physical property data of the present compound and the compounds prepared similarly are shown in Tables 1 and 2.

EXAMPLE 5
Synthesis of N-(2-methoxybenzyl)-N-(N-methylaminocarbonyl)-2-phenoxyaniline To a solution of 751 mg of triphosgene in 14 ml of methylene chloride was added dropwise a solution of 2.03 g of N-(2-methoxylbenzyl)-2-phenoxyaniline and 1.03 g of diisopropylethylamine in 25 ml of methylene chloride with stirring, followed by stirring at room temperature for 5 minutes. Into the solution was blown an excess amount of methylamine with stirring, followed by stirring at room temperature for 5 minutes. After concentration under reduced pressure, the reaction mixture was poured into ethyl acetate, washed with 5% hydrochloric acid, a saturated aqueous sodium bicarbonate solution and a saturated aqueous sodium chloride solution, successively, and dried over anhydrous sodium sulfate. After removal of the drying agent by filtration, the solvent was concentrated under reduced pressure, and the precipitated crystals were recrystallized from ethyl acetate to give 2.02 g of N-(2-methoxybenzyl)-N-(N-methylaminocarbonyl)-2-phenoxyaniline.

The structures and physical property data of the present compound and the compounds prepared similarly are shown in Tables 1 and 2.

EXAMPLE 6
Synthesis of N-(2,5-dimethoxybenzyl)-N-(N-methylaminocarbonyl)-2-phenoxyaniline To a solution of 3.43 ml of acetic acid and 8.36 ml of triethylamine in 90 ml of benzene was added 12.9 ml of diphenylphosphoryl azide, followed by reflux under heating for 2 hours. To the reaction solution was added 2.01 g of N-(2,5-dimethoxybenzyl)-2-phenoxyaniline synthesized in the same manner as in Example 2(1), followed by reflux under heating for 6 hours. The reaction mixture was poured into water, and the organic phase was separated, washed with 5% hydrochloric acid, a saturated aqueous sodium bicarbonate solution and a saturated aqueous sodium chloride solution, successively, and dried over anhydrous sodium sulfate. After removal of the drying agent by filtration, the solvent was concentrated under reduced pressure, and the residue was purified by silica gel column chromatography (eluent; ethyl acetate-hexane=1:2) and recrystallized from diethyl ether to give 1.20 g of N-(2,5-dimethoxybenzyl)-N-(N-methylaminocarbonyl)-2-phenoxyaniline.

The structures and physical property data of the present compound and the compounds prepared similarly are shown in Tables 1 and 2.

EXAMPLE 7
Synthesis of N-(2-methoxybenzyl)-N-methoxycarbonyl-2-phenoxyaniline (1) To a solution of 775 mg of triphosgene in 14 ml of methylene chloride was added gradually dropwise a solution of 2.16 g of N-(2-methoxybenzyl)-2-phenoxyaniline and 1.10 g of diisopropylethylamine in 25 ml of methylene chloride with stirring, followed by stirring at room temperature for 15 minutes. The reaction mixture was concentrated under reduced pressure, poured into ethyl acetate, washed with 5% hydrochloric acid, a saturated aqueous sodium bicarbonate solution and a saturated aqueous sodium chloride solution, successively, and dried over anhydrous sodium sulfate. After removal of the drying agent by filtration, the solvent was concentrated under reduced pressure, and the residue was purified by silica gel column chromatography (eluent; ethyl acetate-hexane=1:15) to give 2.57 g of N-chlorocarbonyl-N-(2-methoxybenzyl)-2-phenoxyaniline.

(2) To a solution of 226 mg of sodium methoxide in 5 ml of tetrahydrofuran was added dropwise a solution of 1.22 g of N-chlorocarbonyl-N-(2-methoxybenzyl)-2-phenoxyaniline in 5 ml of tetrahydrofuran under ice-cooling with stirring, followed by stirring at room temperature for 20 minutes. The reaction mixture was concentrated under reduced pressure, poured into water and extracted with ethyl acetate, and the extract was washed with 5% hydrochloric acid, a saturated aqueous sodium bicarbonate solution and a saturated aqueous sodium chloride solution, successively, and dried over anhydrous sodium sulfate. After removal of the drying agent by filtration, the solvent was concentrated under reduced pressure, and the residue was purified by silica gel column chromatography (eluent; ethyl acetate-hexane=1:6) and recrystallized from ethyl acetate to give 1.18 g of N-(2-methoxybenzyl)-N-methoxycarbonyl-2-phenoxyaniline.

The structures and physical property data of the present compound and the compounds prepared similarly are shown in Tables 1 and 2.

EXAMPLE 8
Synthesis of N-aminoacetyl-N-(2-methoxybenzyl)-2-phenoxyaniline (1) A solution of 1.51 g of N-chloroacetyl-N-(2-methoxybenzyl)-2-phenoxyaniline synthesized in the same manner as in Example 1 and 770 mg of sodium azide in 10 ml of dimethylformamide was stirred at room temperature overnight. The reaction mixture was poured into water and extracted with ethyl acetate. The extract was washed with 5% hydrochloric acid, a saturated aqueous sodium bicarbonate solution and a saturated aqueous sodium chloride solution, successively, and dried over anhydrous sodium sulfate. After removal of the drying agent by filtration, the solvent was concentrated under reduced pressure, and the residue was purified by silica gel column chromatography (eluent; ethyl acetate-hexane=1:4) to give 1.55 g of N-azidoacetyl-N-(2-methoxybenzyl)-2-phenoxyaniline as an oil.

(2) To a solution of 647 mg of N-azidoacetyl-N-(2-methoxybenzyl)-2-phenoxyaniline in 7 ml of methanol was added 20 mg of platinum oxide, followed by stirring under a hydrogen atmosphere at room temperature overnight. The reaction mixture was filtered through Celite, and after concentration under reduced pressure, purified by silica gel column chromatography (eluent; ethyl acetate-hexane=1:6) and recrystallized from ethyl acetate-isopropyl ether to give 0.24 g of N-aminoacetyl-N-(2-methoxybenzyl)-2-phenoxyaniline.

The structures and physical property data of the present compound and the compounds prepared similarly are shown in Tables 1 and 2.

EXAMPLE 9
Synthesis of N-hydroxyacetyl-N-(2-methoxybenzyl)-2-phenoxyaniline (1) In 10 ml of benzene were stirred 1.01 g of N-chloroacetyl-N-(2-methoxybenzyl)-2-phenoxyaniline, 1.30 g of sodium acetate and 170 mg of tetra-n-butyl ammonium bromide at 80° C. for 5 hours. The reaction mixture was poured into ethyl acetate, washed with water and a saturated aqueous sodium chloride solution, successively, and dried over anhydrous sodium sulfate. After removal of the drying agent by filtration, the solvent was concentrated under reduced pressure, and the residue was purified by silica gel column chromatography (eluent; ethyl acetate-hexane=1:3) to give 1.03 g of N-acetoxyacetyl-N-(2-methoxybenzyl)-2-phenoxyaniline as an oil.

(2) In 6 ml of methanol was dissolved 525 mg of N-acetoxyacetyl-N-(2-methoxybenzyl)-2-phenoxyaniline, and then 537 mg of potassium carbonate was added, followed by stirring at 50° C. for 7 hours. The reaction mixture was poured into water and extracted with ethyl acetate. The extract was washed with 5% hydrochloric acid, a saturated aqueous sodium bicarbonate solution and a saturated aqueous sodium chloride solution, successively, and dried over anhydrous sodium sulfate. After removal of the drying agent by filtration, the solvent was concentrated under reduced pressure, and the residue was purified by silica gel column chromatography (eluent; ethyl acetate-hexane=1:3) and allowed to stand at room temperature to give 450 mg of N-hydroxyacetyl-N-(2-methoxybenzyl)-2-phenoxyaniline as crystals.

The structures and physical property data of the present compound and the compounds prepared similarly are shown in Tables 1 and 2.

EXAMPLE 10
Synthesis of N-acetyl-N-(2-pyrrolidinobenzyl)-2-phenoxyaniline monohydrochloride (1) In 80 ml of methanol was dissolved 8.00 g of N-acetyl-N-(2-nitrobenzyl)-2-phenoxyaniline synthesized in the same manner as in Example 3, and then 66 mg of platinum dioxide was added, followed by stirring under a hydrogen atmosphere at room temperature overnight. To the reaction mixture was added 40 ml of chloroform for dissolving the precipitate, and the catalyst was removed by filtration. The filtrate was concentrated under reduced pressure, and the residue was recrystallized from methanol to give 6.88 g of N-acetyl-N-(2-aminobenzyl)-2-phenoxyaniline.

(2) In 10 ml of N,N-dimethylformamide were stirred 1.00 g of N-acetyl-N-(2-aminobenzyl)-2-phenoxyaniline, 680 mg of 1,4-dibromobutane, 1.03 g of potassium carbonate and 50 mg of potassium iodide at 70° C. for 3 days. The reaction mixture was poured into water and extracted with ethyl acetate, and the extract was washed with water and a saturated aqueous sodium chloride solution, successively, and dried over anhydrous sodium sulfate. After removal of the drying agent by filtration, the solvent was concentrated under reduced pressure, and the residue was purified by silica gel column chromatography (eluent; ethyl acetate-hexane=1:3). The resulting product was dissolved in 5 ml of ether, and after addition of 0.9 ml of 4 N hydrogen chloride-ethyl acetate, the solution was concentrated and recrystallized from ethyl acetate-ether to give 0.49 g of N-acetyl-N-(2-pyrrolidinobenzyl)-2-phenoxyaniline monohydrochloride.

The structures and physical property data of the present compound and the compounds prepared similarly are shown in Tables 1 and 2.

EXAMPLE 11
Synthesis of N-acetyl-N-(2-carboxymethoxybenzyl)-2-phenoxyaniline (1) In 30 ml of methanol were dissolved 1.74 g of 2-acetoxybenzaldehyde and 1.85 g of 2-phenoxyaniline, and after stirring at room temperature for an hour, 3.00 g of sodium borohydride was added, followed by stirring at the same temperature for 30 minutes. To the reaction solution was added dropwise an aqueous acetic acid solution (3.0 ml of acetic acid and 60 ml of water), and after stirring at room temperature for 10 minutes, the mixture was extracted with ethyl acetate. The extract was washed with a saturated aqueous sodium bicarbonate solution and a saturated aqueous sodium chloride solution, and dried over anhydrous sodium sulfate. After removal of the drying agent by filtration, the solvent was concentrated under reduced pressure. A solution of the residue and 4 ml of triethylamine in 50 ml of methylene chloride was cooled to 0° C., and 2.00 ml of acetyl chloride was added dropwise with stirring, followed by stirring at room temperature for 20 minutes. The reaction mixture was poured into water and extracted with ethyl acetate. The extract was washed with 0.5 N hydrochloric acid, a saturated aqueous sodium bicarbonate solution and a saturated aqueous sodium chloride solution, successively, and dried over anhydrous sodium sulfate. After removal of the drying agent by filtration, the solvent was concentrated under reduced pressure to give a crude N-acetyl-N-(2-acetyloxybenzyl)-2-phenoxyaniline.

This was dissolved in 40 ml of methanol, and 14 ml of 5% aqueous potassium hydroxide solution was added, followed by stirring at room temperature for an hour. The reaction mixture was concentrated under reduced pressure, poured into water and extracted with ethyl acetate. The extract was washed with 5% hydrochloric acid, a saturated aqueous sodium bicarbonate solution and a saturated aqueous sodium chloride solution, successively, and dried over anhydrous sodium sulfate. After removal of the drying agent by filtration, the solvent was concentrated under reduced pressure, and the residue was crystallized from diisopropyl ether to give 1.86 g of N-acetyl-N-(2-hydroxybenzyl)-2-phenoxyaniline.

(2) To a solution of 666 mg of N-acetyl-N-(2-hydroxybenzyl)-2-phenoxyaniline in 10 ml of N,N-dimethylformamide was added 80 mg of 60% NaH/oil, followed by stirring at room temperature for 30 minutes. To this was added 0.3 ml of methyl bromoacetate, followed by stirring at room temperature for 30 minutes. The reaction solution was poured into 0.5 N hydrochloric acid and extracted with ethyl acetate. The extract was washed with 0.5 N hydrochloric acid, a saturated aqueous sodium bicarbonate solution and a saturated aqueous sodium chloride solution, successively, and dried over anhydrous sodium sulfate. After filtration, the filtrate was concentrated under reduced pressure to give a crude N-acetyl-N-(2-methoxycarbonylmethoxybenzyl)-2-phenoxyaniline.

This was dissolved in 10 ml of methanol, and 5% aqueous potassium hydroxide solution was added and stirred at room temperature for an hour. The reaction solution was made acidic with 2 N hydrochloric acid and extracted with ethyl acetate, and the extract was washed with a saturated aqueous sodium chloride solution and dried over anhydrous sodium sulfate. After removal of the drying agent by filtration, the solvent was concentrated under reduced pressure, and the residue was crystallized from diisopropyl ether to give 745 mg of N-acetyl-N-(2-carboxymethoxybenzyl)-2-phenoxyaniline.

The structures and physical property data of the present compound and the compounds prepared similarly are shown in Tables 1 and 2.

EXAMPLE 12

Synthesis of N-acetyl-N-(2-propylbenzyl)-2-phenoxyaniline (1) In 40 ml of acetone was dissolved 2.81 g of N-acetyl-N-[2-(1,3-dioxolan-2-yl)benzyl]-2-phenoxyaniline synthesized in the same manner as in Example 3, and then 0.10 g of p-toluenesulfonic acid monohydrate was added, followed by stirring at room temperature for 6 hours. To the reaction solution was added a saturated aqueous sodium bicarbonate solution, the acetone was concentrated under reduced pressure, and the residue was extracted with ethyl acetate, washed with a saturated aqueous sodium bicarbonate solution and a saturated aqueous sodium chloride solution and dried over anhydrous sodium sulfate. After removal of the drying agent by filtration, the solvent was concentrated under reduced pressure, and the residue was purified by silica gel column chromatography (eluent; ethyl acetate-hexane=1:3), dried and allowed to stand at room temperature to give 2.12 g of N-acetyl-N-(2-formylbenzyl)-2-phenoxyaniline as crystals.

(2) To a suspension of 4.34 g of ethyltriphenylphosphonium bromide in 20 ml of tetrahydrofuran was added dropwise 6.63 ml of 1.63 M n-butyl lithium/hexane solution under a nitrogen stream, while keeping the temperature of the reaction solution at −15 to −10° C. The temperature of the reaction solution was gradually raised to room temperature, and after stirring at room temperature for 20 minutes, a solution of 1.01 g of N-acetyl-N-(2-formylbenzyl)-2-phenoxyaniline in 10 ml of tetrahydrofuran was added dropwise, followed by further stirring for an hour. After addition of a saturated aqueous ammonium chloride solution, the reaction solution was extracted with ethyl acetate, and the extract was washed with a saturated aqueous sodium chloride solution and dried over anhydrous sodium sulfate. After removal of the drying agent by filtration, the solvent was concentrated under reduced pressure to give 859 mg of N-acetyl-N-[2-(propen-1-yl)benzyl]-2-phenoxyaniline as an oil in a mixture of the geometrical isomers at a ratio of about 3:2.

(3) In 7 ml of ethanol was dissolved 757 mg of N-acetyl-N-[2-(propen-1-yl)benzyl]-2-phenoxyaniline (a mixture of the geometrical isomers at a ratio of about 3:2), and 15 mg of platinum oxide was added, followed by stirring under a hydrogen atmosphere at room temperature for 3 hours. The catalyst in the reaction solution was removed by filtration, the solvent was concentrated under reduced pressure, and the residue was purified by silica gel column chromatography (eluent; ethyl acetate-hexane=1:4) to give 647 mg of N-acetyl-N-(2-propylbenzyl)-2-phenoxyaniline as an oil.

The structures and physical property data of the present compound and the compounds prepared similarly are shown in Tables 1 and 2.

EXAMPLE 13

Synthesis of N-acetyl-N-(2-acetylbenzyl)-2-phenoxyaniline (1) To an ice-cooled solution of 5.25 ml of 1M methylmagnesium chloride/tetrahydrofuran diluted with 15 ml of tetrahydrofuran was added dropwise a solution of 1.20 g of N-acetyl-N-(2-formylbenzyl)-2-phenoxyaniline in 7 ml of tetrahydrofuran, followed by stirring at room temperature for an hour. The reaction solution was again cooled on ice, and after addition of a saturated aqueous ammonium chloride solution, extracted with ethyl acetate, and the extract was washed with a saturated aqueous sodium chloride solution and dried over anhydrous sodium sulfate. After removal of the drying agent by filtration, the solvent was concentrated under reduced pressure, and the residue was purified by silica gel column chromatography (eluent; ethyl acetate-hexane=1:1) to give 1.19 g of N-acetyl-N-[2-(1-hydroxyethyl)benzyl]-2-phenoxyaniline as an oil.

(2) A solution of 0.22 ml of oxalyl chloride in 13.5 ml of dichloromethane was cooled to −70° C. or below on dry-ice-acetone, and a solution of 0.24 ml of dimethyl sulfoxide in 0.9 ml of dichloromethane was added dropwise, followed by stirring for 10 minutes. To this was added dropwise a solution of 0.48 g of N-acetyl-N-[2-(1-hydroxyethyl)benzyl]-2-phenoxyaniline in 4.5 ml of dichloromethane, and the temperature of the reaction solution was gradually raised to −45° C., followed by stirring at the same temperature for an hour. To the reaction solution was added dropwise 1.34 ml of triethylamine at −40° C. or below, followed by stirring at 0° C. for 20 minutes. The reaction solution, after addition of a saturated aqueous ammonium chloride solution, was extracted with ethyl acetate, and the extract was washed with a saturated aqueous sodium chloride solution and dried over anhydrous sodium sulfate. After removal of the drying agent by filtration, the solvent was concentrated under reduced pressure, and the residue was purified by silica gel column chromatography (eluent; ethyl acetate-hexane=1:1) and recrystallized from ethyl acetate-hexane to give 0.41 g of N-acetyl-N-(2-acetylbenzyl)-2-phenoxyaniline.

The structures and physical property data of the present compound and the compounds prepared similarly are shown in Tables 1 and 2.

EXAMPLE 14

Synthesis of N-acetyl-N-(2-dimethylaminocarbonylbenzyl)-2-phenoxyaniline (1) To a mixture of 23 ml of methanol and 3.6 ml of 2 N aqueous potassium hydroxide solution was added 2.26 g of N-acetyl-N-(2-methoxycarbonylbenzyl)-2-phenoxyaniline synthesized in the same manner as in Example 2, followed by stirring at 60° C. for an hour. The reaction mixture was concentrated under reduced pressure, water was added to the residue, and the mixture was made acidic with 2 N hydrochloric acid and extracted with ethyl acetate. The extract was washed with a saturated aqueous sodium chloride solution and dried over anhydrous sodium sulfate. After removal of the drying agent by filtration, the solvent was concentrated under reduced pressure, and the residue was purified by silica gel column chromatography (eluent; ethyl acetate-hexane=1:1) to give 2.01 g of N-acetyl-N-(2-carboxybenzyl)-2-phenoxyaniline as an oil.

(2) In a mixture of 10 ml of tetrahydrofuran and 0.1 ml of hexamethylphosphoramide was dissolved 0.50 g of N-acetyl-N-(2-carboxybenzyl)-2-phenoxyaniline, and 0.2 ml of thionyl chloride was added, followed by stirring at room temperature for 3 hours. The reaction mixture was concentrated, the residue was dissolved in 10 ml of tetrahydrofuran, and 2 ml of 50% aqueous dimethylamine solution was added dropwise with stirring. The reaction mixture was poured into water and extracted with ethyl acetate, and the extract was washed with 1 N hydrochloric acid, a saturated aqueous sodium bicarbonate solution and a saturated aqueous sodium chloride solution, successively, and dried over anhydrous sodium sulfate. After removal of the drying agent by filtration, the solvent was concentrated under reduced pressure, and the residue was purified by silica gel column chromatography (eluent; ethyl acetate-hexane=1:3) to give 0.49 g of N-acetyl-N-(2-dimethylaminocarbonylbenzyl)-2-phenoxyaniline as an oil.

The structures and physical property data of the present compound and the compounds prepared similarly are shown in Tables 1 and 2.

EXAMPLE 15
Synthesis of N-acetyl-N-(2-ethoxycarbonylbenzyl)-2-phenoxyaniline In 10 ml of N,N-dimethylformamide were stirred 0.50 g of N-acetyl-N-(2-carboxybenzyl)-2-phenoxyaniline, 0.20 g of anhydrous potassium carbonate and 0.22 ml of diethyl sulfate at room temperature for 3 hours. The reaction mixture was poured into water and extracted with ethyl acetate, and the extract was washed with 1 N hydrochloric acid, a saturated aqueous sodium bicarbonate solution and a saturated aqueous sodium chloride solution, successively, and dried over anhydrous sodium sulfate. After removal of the drying agent by filtration, the solvent was concentrated under reduced pressure, and the residue was purified by silica gel column chromatography (eluent; ethyl acetate-hexane=1:7) to give 0.50 g of N-acetyl-N-(2-ethoxycarbonylbenzyl)-2-phenoxyaniline as an oil.

The structures and physical property data of the present compound and the compounds prepared similarly are shown in Tables 1 and 2.

EXAMPLE 16
Synthesis of N-acetyl-N-(2-methoxyphenyl)-2-phenoxyaniline

In 20 ml of nitrobenzene were refluxed 2.27 g of N-acetyl-2-phenoxyaniline, 1.3 ml of 2-iodoanisole, 1.38 g of potassium carbonate, 133 mg of a copper powder and 200 mg of copper bromide under heating for 8 hours. The reaction solution was cooled to room temperature, and after addition of ethyl acetate, the insoluble matter was removed by filtration. The filtrate was washed with 0.5 N hydrochloric acid, a saturated aqueous sodium bicarbonate solution and a saturated aqueous sodium chloride solution, successively, and dried over anhydrous sodium sulfate. After removal of the drying agent by filtration, the solvent was concentrated under reduced pressure, and the residue was purified by silica gel column chromatography (eluent; ethyl acetate-hexane=1:4) to give 660 mg of N-acetyl-N-(2-methoxyphenyl)-2-phenoxyaniline as an oil.

The structures and physical property data of the present compound and the compounds prepared similarly are shown in Tables 1 and 2.

EXAMPLE 17
Synthesis of N-acetyl-N-[2-(2-methoxyphenyl)ethyl]-2-phenoxyaniline (1) In 30 ml of toluene were dissolved 4.98 g of 2-methoxyphenylacetic acid and 0.5 ml of N,N-dimethylformamide, and then 4 ml of thionyl chloride was added.

To a solution of 4.98 g of 2-methoxyphenylacetic acid and 0.5 ml of N,N-dimethylformamide in 30 ml of toluene was added 4 ml of thionyl chloride, and after stirring at 70° C. for an hour, the mixture was concentrated under reduced pressure. The residue was dissolved in 20 ml of methylene chloride and added dropwise to an ice-cooled solution of 5.55 g of 2-phenoxyaniline and 4.6 ml of triethylamine in 30 ml of methylene chloride with stirring, followed by stirring at room temperature for an hour. The reaction solution was concentrated under reduced pressure, and after addition of ice-water, extracted with ethyl acetate, and the extract was washed with 0.5 N hydrochloric acid, a saturated aqueous sodium bicarbonate solution and a saturated aqueous sodium chloride solution, successively, and dried over anhydrous sodium sulfate. After removal of the drying agent by filtration, the solvent was concentrated under reduced pressure.

The residue was dissolved in 40 ml of tetrahydrofuran and added dropwise to a suspension of 1.70 g of aluminum lithium hydride in 40 ml of tetrahydrofuran, followed by reflux under heating for 30 minutes. The reaction mixture was cooled with ice-water, and a saturated aqueous sodium sulfate solution was added dropwise with stirring. The insoluble matter in the reaction solution was removed by filtration through an anhydrous magnesium sulfate plate, the filtrate was concentrated under reduced pressure, and the residue was purified by silica gel column chromatography (eluent; ethyl acetate-hexane=1:10) to give 8.23 g of N-[2-(2-methoxyphenyl)ethyl]-2-phenoxyaniline as an oil.

(2) The same reaction and working-up as in Example 1(2) were carried out using 3.19 g of N-[2-(2-methoxyphenyl)ethyl]-2-phenoxyaniline, and crystallization from hexane gave 2.95 g of N-acetyl-N-[2-(2-methoxyphenyl)ethyl]-2-phenoxyaniline.

The structures and physical property data of the present compound and the compounds prepared similarly are shown in Tables 1 and 2.

TABLE 1

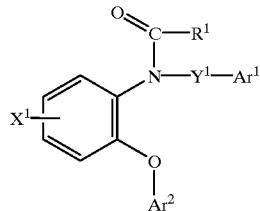

| Comp. No.*[1] | Exp. No.*[2] | Ar[1]—Y[1] | Ar[2] | R[1] | X[1] | m.p. (° C.) (Recry. Sol.*[3]) |
|---|---|---|---|---|---|---|
| 001 | 3 | 3-MeO—Ph—CH$_2$ | Ph | Me | H | oil*[6] |
| 002 | 3 | 4-MeO—Ph—CH$_2$ | Ph | Me | H | 99.5–100.0 (Hex-Et$_2$O) |
| 003 | 1 | 2-EtO—Ph—CH$_2$ | Ph | Me | H | oil*[6] |
| 004 | 3 | 2-EtO—Ph—CH$_2$ | Ph | Me | 4-Cl | 103.5–104.0 (Hex) |
| 005 | 1 | 2-n-PrO—Ph—CH$_2$ | Ph | Me | H | oil*[6] |

TABLE 1-continued

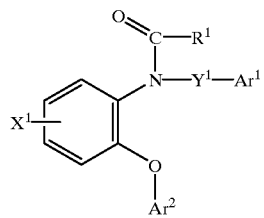

| Comp. No.*1 | Exp. No.*2 | Ar1—Y1 | Ar2 | R1 | X1 | m.p. (° C.) (Recry. Sol.*3) |
|---|---|---|---|---|---|---|
| 006 | 3 | 2-n-PrO—Ph—CH$_2$ | Ph | Me | 4-Cl | 95.5–96.0 (Hex) |
| 007 | 1 | 2-i-PrO—Ph—CH$_2$ | Ph | Me | H | oil*6 |
| 008 | 3 | 2-i-PrO—Ph—CH$_2$ | Ph | Me | 4-Cl | 108.0–108.5 (Hex) |
| 009 | 1 | 2-i-BuO—Ph—CH$_2$ | Ph | Me | H | oil*6 |
| 010 | 1 | 2-n-PenO—Ph—CH$_2$ | Ph | Me | H | oil*6 |
| 011 | 1 | 2-i-PenO—Ph—CH$_2$ | Ph | Me | H | oil*6 |
| 012 | 17 | 2-MeO—Ph—(CH$_2$)$_2$ | Ph | Me | H | 79.0–80.0 (Hex*5) |
| 013 | 16 | 2-MeO—Ph | Ph | Me | H | oil*6 |
| 014 | 2 | 2-MeO—Ph—CH(Me) | Ph | Me | H | 96.5–97.0 (standing*4) |
| 015 | 3 | 2,3-(MeO)$_2$—Ph—CH$_2$ | Ph | Me | H | oil*6 |
| 016 | 2 | 2,4-(MeO)$_2$—Ph—CH$_2$ | Ph | Me | H | oil*6 |
| 017 | 3 | 2,5-(MeO)$_2$—Ph—CH$_2$ | Ph | Me | H | oil*6 |
| 018 | 3 | 2,5-(MeO)$_2$—Ph—CH$_2$ | Ph | Me | 4-Me | oil*6 |
| 019 | 3 | 2,5-(MeO)$_2$—Ph—CH$_2$ | Ph | Me | 5-Me | 108.0–109.0 (standing*4) |
| 020 | 3 | 2,5-(MeO)$_2$—Ph—CH$_2$ | Ph | Me | 4-F | oil*6 |
| 021 | 3 | 2,5-(MeO)$_2$—Ph—CH$_2$ | Ph | Me | 5-F | 92.5–93.5 (IPE) |
| 022 | 3 | 2,5-(MeO)$_2$—Ph—CH$_2$ | Ph | Me | 4-Cl | 103.0–105.0 (IPE) |
| 023 | 3 | 2,5-(MeO)$_2$—Ph—CH$_2$ | Ph | Me | 5-Cl | 114.0–114.5 (IPE) |
| 024 | 2 | 2,6-(MeO)$_2$—Ph—CH$_2$ | Ph | Me | H | oil*6 |
| 025 | 3 | 3,5-(MeO)$_2$—Ph—CH$_2$ | Ph | Me | H | oil*6 |
| 026 | 2 | 2,4,6-(MeO)$_3$—Ph—CH$_2$ | Ph | Me | H | 122.0–123.0 (AcOEt-Hex) |
| 027 | 11 | 2-HO—Ph—CH$_2$ | Ph | Me | H | 123.0–124.5 (IPE*5) |
| 028 | 11 | 2-MeCOO—Ph—CH$_2$ | Ph | Me | H | oil*6 |
| 029 | 3 | 2-Cl—Ph—CH$_2$ | Ph | Me | H | oil*6 |
| 030 | 3 | 3-Cl—Ph—CH$_2$ | Ph | Me | H | oil*6 |
| 031 | 3 | 4-Cl—Ph—CH$_2$ | Ph | Me | H | 92.0–93.0 (Hex-Et$_2$O) |
| 032 | 3 | 2-F—Ph—CH$_2$ | Ph | Me | H | 90.0–90.5 (IPE) |
| 033 | 3 | 2-Br—Ph—CH$_2$ | Ph | Me | H | 84.0–84.5 (IPE) |
| 034 | 3 | 2-MeS—Ph—CH$_2$ | Ph | Me | H | oil*6 |
| 035 | 11 | 2-HO$_2$CCH$_2$O—Ph—CH$_2$ | Ph | Me | H | 156.5–157.0 (IPE*5) |
| 036 | 11 | 2-HO$_2$CC(Me)$_2$O—Ph—CH$_2$ | Ph | Me | H | 65.0–67.0 (standing*4) |
| 037 | 1 | 2-(Me$_2$N(CH$_2$)$_2$O)—Ph—CH$_2$ | Ph | Me | H | oil*6 |
| 038 | 13 | 2-CH$_3$(HO)CH—Ph—CH$_2$ | Ph | Me | H | oil*6 |
| 039 | 13 | 2-Et(HO)CH—Ph—CH$_2$ | Ph | Me | H | oil*6 |
| 040 | 2 | 2-MeO$_2$C—Ph—CH$_2$ | Ph | Me | H | 76.0–78.0 (IPE) |
| 041 | 15 | 2-EtO$_2$C—Ph—CH$_2$ | Ph | Me | H | oil*6 |
| 042 | 14 | 2-HO$_2$C—Ph—CH$_2$ | Ph | Me | H | oil*6 |
| 043 | 14 | 2-MeNHCO—Ph—CH$_2$ | Ph | Me | H | oil*6 |
| 044 | 14 | 2-Me$_2$NCO—Ph—CH$_2$ | Ph | Me | H | oil*6 |
| 045 | 3 | 2-(—O(CH$_2$)$_2$O—)CH—Ph—CH$_2$ | Ph | Me | H | oil*6 |
| 046 | 12 | 2-OHC—Ph—CH$_2$ | Ph | Me | H | 114.0–117.0 (standing*4) |
| 047 | 13 | 2-CH$_3$CO—Ph—CH$_2$ | Ph | Me | H | 110.0–110.5 (AcOEt-Hex) |
| 048 | 13 | 2-EtCO—Ph—CH$_2$ | Ph | Me | H | oil*6 |
| 049 | 1 | 2-Me—Ph—CH$_2$ | Ph | Me | H | 83.5–84.0 (IPE) |
| 050 | 12 | 2-n-Pr—Ph—CH$_2$ | Ph | Me | H | oil*6 |
| 051 | 12 | 2-CH$_2$=CH—Ph—CH$_2$ | Ph | Me | H | oil*6 |
| 052 | 1 | 2-NO$_2$—Ph—CH$_2$ | Ph | Me | H | 96.0–96.5 (AcOEt-Hex) |
| 053 | 10 | 2-NH$_2$—Ph—CH$_2$ | Ph | Me | H | 155.5–156.0 (MeOH) |
| 054 | 10 | 2-pyrrolidino-Ph—CH$_2$ | Ph | Me | H | 110.0–112.5*7 (AcOEt—Et$_2$O) |
| 055 | 2 | 4-Me$_2$N—Ph—CH$_2$ | Ph | Me | H | oil*6 |
| 056 | 3 | Ph—CH$_2$ | Ph | Me | H | 80.5–81.0 (Et$_2$O) |
| 057 | 3 | 2-Py—CH$_2$ | Ph | Me | H | 86.5–87.5 (Et$_2$O) |
| 058 | 3 | 3-Py—CH$_2$ | Ph | Me | H | 83.5–84.0 (IPE) |
| 059 | 3 | 4-Py—CH$_2$ | Ph | Me | H | 114.5–115.0 (Et$_2$O) |
| 060 | 1 | 3-MeO-2-Py—CH$_2$ | Ph | Me | H | 95.0–96.0 (standing*4) |
| 061 | 1 | 2-MeO-3-Py—CH$_2$ | Ph | Me | H | 78.5–79.0 (IPE-Hex) |
| 062 | 1 | 4-MeO-3-Py—CH$_2$ | Ph | Me | H | 90.5–91.0 (standing*4) |
| 063 | 2 | 2-MeO—Ph—CH$_2$ | 1-Naph | Me | H | 66.0–68.0 (AcOEt-Hex) |
| 064 | 3 | 2-MeO—Ph—CH$_2$ | Ph | Et | H | oil*6 |
| 065 | 3 | 2-MeO—Ph—CH$_2$ | Ph | Et | 4-Cl | oil*6 |
| 066 | 3 | 2-EtO—Ph—CH$_2$ | Ph | Et | 4-Cl | 81.5–83.0 (Hex) |
| 067 | 3 | 2-n-PrO—Ph—CH$_2$ | Ph | Et | 4-Cl | 87.5–88.0 (Hex) |
| 068 | 3 | 2-i-PrO—Ph—CH$_2$ | Ph | Et | 4-Cl | oil*6 |
| 069 | 3 | 2,5-(MeO)$_2$—Ph—CH$_2$ | Ph | Et | 4-Cl | oil*6 |

TABLE 1-continued

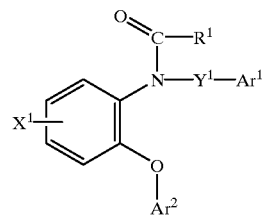

| Comp. No.*1 | Exp. No.*2 | Ar$^1$—Y$^1$ | Ar$^2$ | R$^1$ | X$^1$ | m.p. (° C.) (Recry. Sol.*3) |
|---|---|---|---|---|---|---|
| 070 | 2 | 2-MeO$_2$C—Ph—CH$_2$ | Ph | Et | H | oil*6 |
| 071 | 1 | 2-MeO—Ph—CH$_2$ | Ph | n-Pr | H | oil*6 |
| 072 | 1 | 2-MeO—Ph—CH$_2$ | Ph | i-Pr | H | 94.5–95.0 (Et$_2$O) |
| 073 | 1 | 2-MeO—Ph—CH$_2$ | Ph | n-Bu | H | oil*6 |
| 074 | 1 | 2-MeO—Ph—CH$_2$ | Ph | i-Bu | H | oil*6 |
| 075 | 1 | 2-MeO—Ph—CH$_2$ | Ph | n-Pen | H | oil*6 |
| 076 | 1 | 2-MeO—Ph—CH$_2$ | Ph | c-Pr | H | 73.0–74.0 (Et$_2$O-Hex) |
| 077 | 1 | 2-MeO—Ph—CH$_2$ | Ph | c-Bu | H | 85.0–86.0 (Et$_2$O-Hex) |
| 078 | 1 | 2-MeO—Ph—CH$_2$ | Ph | c-Pen | H | 92.5–93.5 (Et$_2$O-Hex) |
| 079 | 1 | 2-MeO—Ph—CH$_2$ | Ph | Ph | H | 125.5–127.0 (AcOEt-Hex) |
| 080 | 1 | 2-MeO—Ph—CH$_2$ | Ph | F$_3$C | H | oil*6 |
| 081 | 1 | 2-MeO—Ph—CH$_2$ | Ph | ClCH$_2$ | H | 83.0–83.5 (standing*4) |
| 082 | 9 | 2-MeO—Ph—CH$_2$ | Ph | AcOCH$_2$ | H | oil*6 |
| 083 | 8 | 2-MeO—Ph—CH$_2$ | Ph | N$_3$CH$_2$ | H | oil*6 |
| 084 | 8 | 2-MeO—Ph—CH$_2$ | Ph | NH$_2$CH$_2$ | H | 85.0–86.0 (AcOEt-IPE) |
| 085 | 9 | 2-MeO—Ph—CH$_2$ | Ph | HOCH$_2$ | H | 70.0–71.0 (standing*4) |
| 086 | 1 | 2-MeO—Ph—CH$_2$ | Ph | HO$_2$C(CH$_2$) | H | 136.5–138.5 (AcOEt-Hex) |
| 087 | 3 | 2-MeO—Ph—CH$_2$ | Ph | H | H | oil*6 |
| 088 | 3 | 2-EtO—Ph—CH$_2$ | Ph | H | H | oil*6 |
| 089 | 4 | 2-MeO—Ph—CH$_2$ | Ph | NH$_2$ | H | 89.5–90.0 (AcOEt) |
| 090 | 5 | 2-MeO—Ph—CH$_2$ | Ph | NHMe | H | 133.0–134.0 (AcOEt) |
| 091 | 5 | 2-EtO—Ph—CH$_2$ | Ph | NHMe | H | 85.0–86.0 (AcOEt-IPE) |
| 092 | 5 | 2-n-PrO—Ph—CH$_2$ | Ph | NHMe | H | 82.0–83.0 (AcOEt-IPE) |
| 093 | 5 | 2-i-PrO—Ph—CH$_2$ | Ph | NHMe | H | 99.0–99.5 (AcOEt-IPE) |
| 094 | 6 | 2-n-PenO—Ph—CH$_2$ | Ph | NHMe | H | 82.5–83.5 (Et$_2$O) |
| 095 | 6 | 2,5-(MeO)$_2$—Ph—CH$_2$ | Ph | NHMe | H | 88.5–89.5 (Et$_2$O) |
| 096 | 5 | 2-MeO$_2$C—Ph—CH$_2$ | Ph | NHMe | H | 107.0–108.0 (standing*4) |
| 097 | 5 | 2-MeO—Ph—CH$_2$ | Ph | NMe$_2$ | H | 94.5–95.0 (standing*4) |
| 098 | 7 | 2-MeO—Ph—CH$_2$ | Ph | OMe | H | oil*6 |
| 099 | 7 | 2-MeO—Ph—CH$_2$ | Ph | OEt | H | oil*6 |
| 100 | 2 | 2-MeO—Ph—CH$_2$ | 2-Me—Ph | Me | H | oil*6 |
| 101 | 2 | 2-MeO—Ph—CH$_2$ | 3-Me—Ph | Me | H | oil*6 |
| 102 | 2 | 2-MeO—Ph—CH$_2$ | 4-Me—Ph | Me | H | 79.0–80.0 (AcOEt-Hex) |
| 103 | 2 | 2-MeO—Ph—CH$_2$ | 2-MeO—Ph | Me | H | oil*6 |
| 104 | 2 | 2-MeO—Ph—CH$_2$ | 3-MeO—Ph | Me | H | oil*6 |
| 105 | 2 | 2-MeO—Ph—CH$_2$ | 4-MeO—Ph | Me | H | oil*6 |
| 106 | 2 | 2-MeO—Ph—CH$_2$ | 4-MeS—Ph | Me | H | 97.0–98.0 (Et$_2$O-Hex) |
| 107 | 2 | 2-MeO—Ph—CH$_2$ | 2-F—Ph | Me | H | 104.0–105.0 (AcOEt-Hex) |
| 108 | 2 | 2-MeO—Ph—CH$_2$ | 3-F—Ph | Me | H | 54.0–55.0 (AcOEt-Hex) |
| 109 | 2 | 2-MeO—Ph—CH$_2$ | 4-F—Ph | Me | H | oil*6 |
| 110 | 2 | 2-MeO—Ph—CH$_2$ | 4-Cl—Ph | Me | H | 62.0–63.0 (Et$_2$O-Hex) |
| 111 | 2 | 2-MeO—Ph—CH$_2$ | 4-Br—Ph | Me | H | 116.0–117.0 (AcOEt-Hex) |
| 112 | 2 | 2-MeO—Ph—CH$_2$ | 2,4-F$_2$—Ph | Me | H | 81.0–82.0 (Et$_2$O-Hex) |
| 113 | 2 | 2-MeO—Ph—CH$_2$ | 2-Py | Me | H | 81.0–82.0 (Et$_2$O) |
| 114 | 2 | 2-MeO—Ph—CH$_2$ | 3-Py | Me | H | 64.0–65.0 (AcOEt-Hex) |
| 115 | 2 | 2-MeO—Ph—CH$_2$ | 4-Py | Me | H | 93.0–94.0 (Et$_2$O) |
| 116 | 3 | 2-MeO—Ph—CH$_2$ | Ph | Me | 4-F | 83.5–84.0 (AcOEt-Hex) |
| 117 | 3 | 2-MeO—Ph—CH$_2$ | Ph | Me | 5-F | 91.5–92.0 (AcOEt-Hex) |
| 118 | 3 | 2-MeO—Ph—CH$_2$ | Ph | Me | 6-F | oil*6 |
| 119 | 3 | 2-MeO—Ph—CH$_2$ | Ph | Me | 3-Cl | 105.5–106.5 (AcOEt-Hex) |
| 120 | 3 | 2-MeO—Ph—CH$_2$ | Ph | Me | 4-Cl | 113.0–114.5 (AcOEt-Hex) |
| 121 | 3 | 2-MeO—Ph—CH$_2$ | Ph | Me | 5-Cl | 109.0–109.5 (AcOEt-Hex) |
| 122 | 3 | 2-MeO—Ph—CH$_2$ | Ph | Me | 3-Me | 84.5–85.5 (AcOEt-Hex) |
| 123 | 3 | 2-MeO—Ph—CH$_2$ | Ph | Me | 4-Me | 107.5–108.0 (AcOEt-Hex) |
| 124 | 3 | 2-MeO—Ph—CH$_2$ | Ph | Me | 5-Me | 81.5–82.0 (AcOEt-Hex) |
| 125 | 3 | 2-MeO—Ph—CH$_2$ | Ph | Me | 5-CF$_3$ | 113.0–113.5 (AcOEt-Hex) |
| 126 | 3 | 2-MeO—Ph—CH$_2$ | Ph | Me | 5-MeO | 125.5–126.0 (AcOEt-Hex) |
| 127 | 3 | 2-MeO—Ph—CH$_2$ | Ph | Me | 4-PhO | oil*6 |
| 128 | 2 | 2-i-PrO—Ph—CH$_2$ | 4-Me—Ph | Me | 4-Cl | 95.0–96.0 (Et$_2$O-Hep) |
| 129 | 2 | 2-i-PrO—Ph—CH$_2$ | 4-MeO—Ph | Me | 4-Cl | 53.0–56.0 (Et$_2$O-Hep) |
| 130 | 2 | 2-i-PrO—Ph—CH$_2$ | 4-F—Ph | Me | 4-Cl | 82.0–83.0 (Et$_2$O-Hep) |
| 131 | 2 | 2,5-(MeO)$_2$—Ph—CH$_2$ | 4-Me—Ph | Me | 4-Cl | 109.0–110.0 (Et$_2$O-Hep) |
| 132 | 2 | 2,5-(MeO)$_2$—Ph—CH$_2$ | 4-MeO—Ph | Me | 4-Cl | 121.0–122.0 (Et$_2$O-Hep) |
| 133 | 2 | 2,5-(MeO)$_2$—Ph—CH$_2$ | 3-F—Ph | Me | 4-Cl | 79.0–80.0 (Et$_2$O-Hep) |

TABLE 1-continued

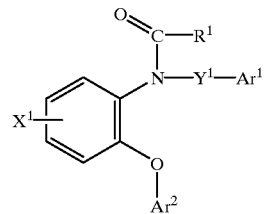

| Comp. No.*1 | Exp. No.*2 | Ar¹—Y¹ | Ar² | R¹ | X¹ | m.p. (° C.) (Recry. Sol.*3) |
|---|---|---|---|---|---|---|
| 134 | 2 | 2,5-(MeO)$_2$—Ph—CH$_2$ | 4-F—Ph | Me | 4-Cl | 102.0–103.0 (Et$_2$O-Hep) |
| 135 | 2 | 2,5-(MeO)$_2$—Ph—CH$_2$ | 4-Me—Ph | Me | 5-Me | 111.0–112.0 (Et$_2$O-Hex) |
| 136 | 2 | 2,5-(MeO)$_2$—Ph—CH$_2$ | 3-F—Ph | Me | 5-Me | 98.0–99.0 (Et$_2$O-Hex) |
| 137 | 2 | 2-i-PrO—Ph—CH$_2$ | 4-F—Ph | Et | 5-Me | 96.0–97.0 (Et$_2$O-Hex) |
| 138 | 2 | 2,5-(MeO)$_2$—Ph—CH$_2$ | 4-MeO—Ph | Et | 5-Me | 85.0–86.0 (Et$_2$O-Hex) |
| 139 | 2 | 2,5-(MeO)$_2$—Ph—CH$_2$ | 4-F—Ph | Et | 5-Me | 79.0–80.0 (Et$_2$O-Hex) |
| 140 | 5 | 2-i-PrO—Ph—CH$_2$ | 3-F—Ph | NHMe | 5-Me | 95.0–96.0 (Et$_2$O-Hex) |
| 141 | 5 | 2-i-PrO—Ph—CH$_2$ | 4-F—Ph | NHMe | 5-Me | 96.0–97.0 (Et$_2$O-Hex) |
| 142 | 5 | 2,5-(MeO)$_2$—Ph—CH$_2$ | 4-Me—Ph | NHMe | 4-Cl | 130.0–131.0 (Et$_2$O) |
| 143 | 5 | 2,5-(MeO)$_2$—Ph—CH$_2$ | 4-MeO—Ph | NHMe | 4-Cl | 153.0–154.0 (Et$_2$O) |
| 144 | 5 | 2,5-(MeO)$_2$—Ph—CH$_2$ | 3-F—Ph | NHMe | 4-Cl | 133.0–134.0 (Et$_2$O) |
| 145 | 5 | 2,5-(MeO)$_2$—Ph—CHZ | 4-F—Ph | NHMe | 4-Cl | 12 7.0–128.0 (Et$_2$O) |
| 146 | 5 | 2,5-(MeO)$_2$—Ph—CH$_2$ | 4-MeO—Ph | NHMe | 5-Me | 119.0–120.0 (Et$_2$O-Hex) |
| 147 | 5 | 2,5-(MeO)$_2$—Ph—CH$_2$ | 3-F—Ph | NHMe | 5-Me | 113.0–114.0 (Et$_2$O-Hex) |
| 148 | 5 | 2,5-(MeO)$_2$—Ph—CH$_2$ | 4-F—Ph | NHMe | 5-Me | 99.0–100.0 (Et$_2$O-Hex) |
| 149 | 2 | 2-MeO—Ph—CH$_2$ | 3-Me$_2$N—Ph | Me | H | 50.0–51.0 (Et$_2$O-Hex) |
| 150 | 2 | 2-MeO—Ph—CH$_2$ | 2-Me$_2$NCH$_2$—Ph | Me | H | oil*6 |
| 151 | 2 | 2-MeO—Ph—CH$_2$ | 3-Me$_2$NCH$_2$—Ph | Me | H | oil*6 |
| 152 | 2 | 2-MeO—Ph—CH$_2$ | 4-Me$_2$NCH$_2$—Ph | Me | H | oil*6 |
| 153 | 2 | 2-MeO—Ph—CH$_2$ | 2-H$_2$NCO—Ph | Me | H | 199.0–200.0 (standing*4) |
| 154 | 3 | 2-MeO—Ph—CH$_2$ | 3-H$_2$NCO—Ph | Me | H | 125.0–127.0 (standing*4) |
| 155 | 3 | 2-MeO—Ph—CH$_2$ | 4-H$_2$NCO—Ph | Me | H | 204.0–206.5 (standing*4) |
| 156 | 1 | 2-MeO—Ph—CH$_2$ | 2-AcHNCO—Ph | Me | H | 169.0–171.0 (standing*4) |
| 157 | 3 | 2-MeO—Ph—CH$_2$ | 4-H$_2$NSO$_2$—Ph | Me | H | 78.0–79.0 (standing*4) |
| 158 | 3 | 2,5-(MeO)$_2$—Ph—CH$_2$ | 4-H$_2$NSO$_2$—Ph | Me | H | 150.0–152.0 (standing*4) |
| 159 | 1 | 2,5-(MeO)$_2$—Ph—CH$_2$ | 2-H$_2$NCO—Ph | Me | H | 184.5–185.5 (standing*4) |
| 160 | 3 | 2,5-(MeO)$_2$—Ph—CH$_2$ | 3-H$_2$NCO—Ph | Me | H | oil*6 |
| 161 | 3 | 2,5-(MeO)$_2$—Ph—CH$_2$ | 4-H$_2$NCO—Ph | Me | H | 178.0–180.0 (standing*4) |
| 162 | 2 | 4-H$_2$NSO$_2$—Ph—CH$_2$ | Ph | Me | H | 143.0–144.0 (EtOH—Et$_2$O) |
| 163 | 2 | 2-H$_2$NSO$_2$—Ph—CH$_2$ | Ph | Me | H | 184.0–185.0 (EtOH) |
| 164 | 2 | 4-H$_2$NSO$_2$-Ph—CH$_2$ | Ph | Me | 5-F | 163.0–165.0 (EtOH) |
| 165 | 2 | 2-H$_2$NSO$_2$—Ph—CH$_2$ | Ph | Me | 5-F | 178.0–179.0 (EtOH) |
| 166 | 2 | 2-HO-5-MeO—Ph—CH$_2$ | Ph | Me | 5-F | 106.0–106.5 (standing*4) |
| 167 | 2 | 2-i-PrO—Ph—CH$_2$ | 3-F—Ph | Me | 4-Cl | oil*6 |
| 168 | 2 | 2-i-PrO—Ph—CH$_2$ | 3-F—Ph | Me | 5-Me | oil*6 |
| 169 | 2 | 2-i-PrO—Ph—CH$_2$ | 4-F—Ph | Me | 5-Me | oil*6 |
| 170 | 2 | 2-i-PrO—Ph—CH$_2$ | 4-Me—Ph | Me | 5-Me | oil*6 |
| 171 | 2 | 2,5-(MeO)$_2$—Ph—CH$_2$ | 4-F—Ph | Me | 5-Me | oil*6 |
| 172 | 2 | 2,5-(MeO)$_2$—Ph—CH$_2$ | 4-MeO—Ph | Me | 5-Me | 102.0–103.0 (AcOEt-Hex) |
| 173 | 3 | 2-MeO—Ph—CH$_2$ | Ph | Me | 5-H$_2$NCO | 250.0–251.0 (standing*4) |
| 174 | 3 | 2,5-(MeO)$_2$—Ph—CH$_2$ | Ph | Me | 5-H$_2$NCO | 168.5–169.0 (standing*4) |
| 175 | 3 | 2-MeO—Ph—CH$_2$ | Ph | Me | 5-H$_2$NSO$_2$ | 192.5–193.5 (standing*4) |
| 176 | 3 | 2,5-(MeO)$_2$—Ph—CH$_2$ | Ph | Me | 5-H$_2$NSO$_2$ | 170.0–171.0 (standing*4) |
| 177 | 17 | 4-Cl—Ph—(CH$_2$)$_2$ | Ph | Me | 5-H$_2$NSO$_2$ | oil*6 |
| 178 | 17 | 2-MeO—Ph—(CH$_2$)$_2$ | Ph | Me | 5-H$_2$NSO$_2$ | oil*6 |
| 179 | 2 | 2-i-PrO—Ph—CH$_2$ | 3-F—Ph | Et | 4-Cl | oil*6 |
| 180 | 2 | 2-i-PrO—Ph—CH$_2$ | 4-F—Ph | Et | 4-Cl | oil*6 |
| 181 | 2 | 2-i-PrO—Ph—CH$_2$ | 4-Me—Ph | Et | 4-Cl | 79.5–80.5 (standing*4) |
| 182 | 2 | 2-i-PrO—Ph—CH$_2$ | 4-MeO—Ph | Et | 4-Cl | 86.0–87.0 (Et$_2$O-Hex) |
| 183 | 2 | 2,5-(MeO)$_2$—Ph—CH$_2$ | 3-F—Ph | Et | 4-Cl | oil*6 |
| 184 | 2 | 2,5-(MeO)$_2$—Ph—CH$_2$ | 4-F—Ph | Et | 4-Cl | oil*6 |
| 185 | 2 | 2,5-(MeO)$_2$—Ph—CH$_2$ | 4-Me—Ph | Et | 4-Cl | 101.0–101.5 (Et$_2$O-Hex) |
| 186 | 2 | 2,5-(MeO)$_2$—Ph—CH$_2$ | 4-MeO—Ph | Et | 4-Cl | oil*6 |
| 187 | 2 | 2-i-PrO—Ph—CH$_2$ | 3-F—Ph | Et | 5-Me | oil*6 |
| 188 | 2 | 2-i-PrO—Ph—CH$_2$ | 4-Me—Ph | Et | 5-Me | 70.0–71.0 (Et$_2$O-Hex) |
| 189 | 2 | 2-i-PrO—Ph—CH$_2$ | 4-MeO—Ph | Et | 5-Me | oil*6 |
| 190 | 2 | 2,5-(MeO)$_2$—Ph—CH$_2$ | 3-F—Ph | Et | 5-Me | 67.0–68.0 (Et$_2$O-Hex) |
| 191 | 2 | 2,5-(MeO)$_2$—Ph—CH$_2$ | 4-Me—Ph | Et | 5-Me | 72.0–73.0 (Et$_2$O-Hex) |
| 192 | 5 | 2-i-PrO—Ph—CH$_2$ | 4-F—Ph | NHMe | 4-Cl | 98.0–99.0 (Et$_2$O-Hex) |
| 193 | 5 | 2-i-PrO—Ph—CH$_2$ | 3-F—Ph | NHMe | 4-Cl | oil*6 |
| 194 | 5 | 2-i-PrO—Ph—CH$_2$ | 4-Me—Ph | NHMe | 4-Cl | oil*6 |
| 195 | 5 | 2-i-PrO—Ph—CH$_2$ | 4-MeO—Ph | NHMe | 4-Cl | oil*6 |
| 196 | 5 | 2-i-PrO—Ph—CH$_2$ | 4-Me—Ph | NHMe | 5-Me | 79.0–80.0 (Et$_2$O-Hex) |
| 197 | 5 | 2-i-PrO—Ph—CH$_2$ | 4-MeO—Ph | NHMe | 5-Me | oil*6 |

TABLE 1-continued

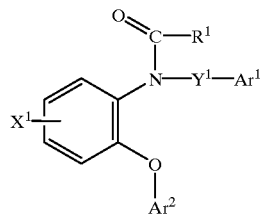

| Comp. No.*[1] | Exp. No.*[2] | Ar[1]—Y[1] | Ar[2] | R[1] | X[1] | m.p. (° C.) (Recry. Sol.*[3]) |
|---|---|---|---|---|---|---|
| 198 | 5 | 2.5-(MeO)$_2$—Ph—CH$_2$ | 4-Me—Ph | NHMe | 5-Me | 84.0–86.0 (Et$_2$O-Hex) |

*[1]Compound Number
*[2]Example Number used for synthesis of the corresponding compound.
*[3]Recrystallization Solvent: Hex = hexane, Et$_2$O = diethyl ether, IPE = diisopropyl ether, AcOEt = ethyl acetate, Hep = heptane.
*[4]Crystallization by Purification by silica gel column chromatography, drying and standing at room temperature.
*[5]Crystallization from the solvent described.
*[6]NMR and MS data of oily substances are shown in Table 2
*[7]Monohydrochloride
Symbols in the table are as follows: Me: methyl, Et: ethyl, Pr: propyl, Bu: butyl, Pen: pentyl, Ph: phenylene, Py: pyridyl, Naph: naphthyl.

TABLE 2

001*[1]:
NMR(CDCl$_3$) δ(ppm) ;1.92(3H, s), 3.73(3H, s), 4.51(1H, d, J = 14.8 Hz),
  5.07(1H, d, J = 14.8 Hz), 6.70~7.37(13H, m)
EIMS m/e;347(M$^+$), 121(M$^+$-226, 100%)
003*[1]:
NMR(CDCl$_3$) δ(ppm) ;1.18(3H, t, J = 7.5 Hz), 1.94(3H, s), 3.66~3.93(2H, m),
  4.72(1H, d, J = 14.5 Hz), 5.17(1H, d, J = 14.5 Hz), 6.68~7.40 (13H, m)
FABMS m/e;362(M$^+$+ 1), 135(M$^+$-226, 100%)
005*[1]:
NMR(CDCl$_3$) δ(ppm) ;0.91 (3H, t, J = 7.3 Hz), 1.53~1.71 (2H, m), 1.93(3H, s),
  3.60~3.81 (2H, m), 4.73(1H, d, J = 14.5 Hz), 5.18(1H, d, J = 14.5 Hz),
  6.69~7.37(13H, m)
FABMS m/e;376(M$^+$+ 1), 149(M$^+$-226, 100%)
007*[1]:
NMR(CDCl$_3$) δ(ppm) ;1.09(3H, d, J = 7.0 Hz), 1.17(3H, d, J = 7.0 Hz), 1.93(3H, s),
  4.26~4.45(1H, m), 4.69(1H, d, J = 14.5 Hz), 5.17(1H, d, J = 14.5 Hz),
  6.71~7.40(13H, m)
FABMS m/e;376(M$^+$+ 1), 149(M$^+$-226, 100%)
009*[1]:
NMR(CDCl$_3$) δ(ppm) ;0.91 (3H, d, J = 6.8 Hz), 0.93(3H, d, J = 6.8 Hz), 1.79~1.98(1H, m),
  1.96(3H, s), 3.45~3.60(2H, m) 4.72(1H d, J = 14.7 Hz), 5.19(1H, d, J = 14.7 Hz),
  6.69~7.36(13H, m)
EIMS m/e;389(M$^+$), 163(M$^+$-226, 100%)
010*[1]:
NMR(CDCl$_3$) δ(ppm) ;0.84~0.96(3H, m), 1.23~1.38(4H, m), 1.50~1.66(2H, m)
  1.95(3H, s), 3.64~3.84(2H, m) 4.70(1H, d, J = 14.6 Hz), 5.17(1H d, J = 14.6 Hz),
  6.70~7.40(13H, m)
EIMS m/e;403(M$^+$), 107(M$^+$-296, 100%)
011*[1]:
NMR(CDCl$_3$) δ(ppm) ;0.87(3H, d, J = 6.6 Hz), 0.88(3H, d, J = 6.6 Hz), 1.41~1.51 (2H, m),
  1.58~1.78(1H, m), 1.95(3H, s), 3.67~3.88(2H, m), 4.69(1H, d, J = 14.7 Hz),
  5.17(1H, d, J = 14.7 Hz), 6.71~7.41 (13H, m)
EIMS m/e;403(M$^+$), 107(M$^+$-296, 100%)
013*[1]:
NMR(CDCl$_3$) δ(ppm) ;1.97(3Hx2/3, s), 2.13(3Hx1/3, s), 3.98(3H, s),
  6.80~7.62(13H, m)
EIMS m/e;333(M$^+$), 291(M$^+$-42, 100%)
015*:1
NMR(CDCl$_3$) δ(ppm) ;1.96(3H; s), 3.53(3H, s), 3.81 (311, s), 4.70(1H, d, J = 14.5 Hz),
  5.27(1H, d, J = 14.5 Hz), 6.73~7.39(12H, m)
FABMS m/e;378(M$^+$+ 1), 151(M$^+$-226, 100%)
016*[1]:
MR(CDCl$_3$) δ(ppm) ;1.92(3H, s), 3.52(3H, s), 3.76(3H, s), 4.65(1H, d, J = 14.4 Hz),
  5.09(1H, d, J = 14.4 Hz), 6.28(1H, d, J = 2.4 Hz), 6.35(1H, dd, J = 8.4, 2.4 Hz),
  6.83~7.36(10H, m)
EIMS m/e;377(M$^+$), 151(M$^+$-226, 100%)

TABLE 2-continued

017*[1]:
NMR(CDCl$_3$) δ(ppm) ;1.96(3H, s), 3.52(3H, s) 3.66(3H, s), 4.70(1H, d, J = 15.0 Hz),
   5.15(1H, d, J = 15.0 Hz), 6.63~7.38(12H, m)
FABMS m/e;378(M$^+$+ 1), 151(M$^+$–226, 100%)
018*[1]:
NMR(CDCl$_3$) δ(ppm) ;1.95(3H, s), 2.23(3H, s), 3.54(3H, s), 3.66(3H, s),
   4.65(1H, d, J = 14.5 Hz), 5.13(1H, d, J = 14.5 Hz), 6.62~~7.40(11H, m)
SIMS m/e;392(M$^+$+ 1), 151(M$^+$–240, 100%)
020*[1]:
NMR(CDCl$_3$) δ(ppm) ;1.96(3H, s), 3.55(3H, s), 3.66(3H, s), 4.70(1H, d, J = 15.0 Hz),
   5.13(1H, d, J = 15.0 Hz), 6.49(1H, dd, J = 9.9, 3.3 Hz), 6.55~7.44(10H, m)
SIMS m/e;396(M$^+$+ 1), 151(M$^+$–244, 100%)
024*[1]:
NMR(CDCl$_3$) δ(ppm) ;1.90(3H, s), 3.56(6H, s), 4.91(1H, d, J = 13.2 Hz),
   5.27(1H, d, J = 13.2 Hz), 6.34~6.43(2H, m), 6.71~~7.35(10H, m)
EIMS m/e;377(M$^+$), 151(M$^+$–226, 100%)
025*[1]:
NMR(CDCl$_3$) δ(ppm) ;1.96(3H, s), 3.67(6H, s), 4.52(1H, d, J = 14.5 Hz),
   5.08(1H, d, J = 14.5 Hz), 6.26~6.39(3H, m), 6.82~7.37(9H, m)
EIMS m/e;377(M$^+$), 151(M$^+$–226, 100%)
028*[1]:
NMR(CDCl$_3$) δ(ppm) ;1.89(3H, s), 2.10(3H, s), 4.38(1H, d, J = 14.0 Hz),
   5.38(1H, d, J = 14.0 Hz), 6.86~7.20(13H, m)
EIMS m/e;375(M$^+$), 185(M$^+$–190, 100%)
029*[1]:
NMR(CDCl$_3$) δ(ppm) ;1.97(3H, s), 4.81 (1H, d, J = 15.0 Hz), 5.29(1H, d, J = 15.0 Hz),
   6.84~7.53(13H, m)
EIMS m/e;353(M$^+$+ 2), 351 (M$^+$), 316(M$^+$–35, 100%)
030*[1]:
NMR(CDCl$_3$) δ(ppm) ;1.96(3H, s), 4.63(1H, d, J = 15.0 Hz), 5.04(1H, d, J = 15.0 Hz),
   6.83~7.39(13H, m)
EIMS m/e;353(M$^+$+ 2), 351 (M$^+$), 258(M$^+$–93, 100%)
034*[1]:
NMR(CDCl$_3$) δ(ppm) ;1.98(3H, s), 2.31(3H, s), 4.75(1H, d, J = 14.8 Hz),
   5.37(1H, d, J = 14.8 Hz), 6; 83~7.38(13H, m)
EIMS m/e;363(M$^+$), 316(M$^+$–47, 100%)
037*[1]:
NMR(CDCl$_3$) δ(ppm) ;1.95(3H, s), 2.26(6H, s), 2.44~2.58(2H, m), 3.74~3.97(2H, m)
   4.72(1H, d, J = 14.7 Hz), 5.17(1H, d, J = 14.7 Hz), 6.71~7.38(13H, m)
FABMS m/e;405(M$^+$+ 1, 100%)
038*hu 1:
NMR(CDCl$_3$) δ(ppm) ;1.34(3Hx1/2, d, J = 6.2 Hz), 1.40(3Hx1/2, d, J = 6.2 Hz),
   1.93(3Hx1/2, s), 1.97(3Hx1/2, s), 4.87(1Hx1/2, d, J = 13.0 Hz),
   4.96(1Hx1/2, d, J = 13.0 Hz), 5.~0(1Hx1/2, d, J = 13.0 Hz),
   5.19 (1Hx1/2, d, J = 13.0 Hz), 6.60~7.51 (13H, m)
EIMS m/e;361(M$^+$), H7(M$^+$–244, 100%)
039*[1]:
NMR(CDCl$_3$) δ(ppm) ;0.88(3Hx1/2, t, J = 7.2 Hz), 0.91 (3Hx1/2, t, J = 7.2 Hz),
   1.40~1.85(2H, m), 1.93(3Hx1/2, s), 1.96(3Hx1/2, s), 4.60~5.40(3H, m),
   6.64~7.42(13H, m)
EIMS m/e;375(M$^+$), 228(M$^+$–147, 100%)
041*[1]:
NMR(CDCl$_3$) δ(ppm) ;1.27(3H, t, J = 7.3 Hz), 1.98(3H, s), 4.18(2H, q, J = 7.3 Hz),
   5.20(1H, d, J = 15.5 Hz), 5.55(1H, d, J = 15.5 Hz), 6.80~7.44(11H, m),
   7.59~7.68(1H, m), 7.74~7.83(1H, m)
EIMS m/e;389(M$^+$), 346(M$^+$–43, 100%)
042*[1]:
NMR(CDCl$_3$) δ(ppm) ;1.99(3H,s), 4.93(1H, d, J = 15.4 Hz), 5.29(~H, d, J = ~5.4 Hz),
   6.92~7.47(11H, m), 7.56~7.60(1H, m), 7.82~7.87(1H, m)
FABMS m/e;362(M$^+$+ 1, 100%)
043*[1]:
NMR(CDCl$_3$) δ(ppm) ;1.95(3H, s), 2.84(3H, d, J = 4.5 Hz), 4.84(1H, d, J = 15.0 Hz),
   5.13(1H, d, J = 15.0 Hz), 6.60~6.78(lH, m), 6.82~7.53(13H, m)
EIMS m/e;374(M$^+$), 300(M$^+$–748 100%)
044*[1]:
NMR(CDCl$_3$) δ(ppm) ; 1.96 (3H, s), 2.62 (3H, s) 3.01 (3H, s), 4.57 (1H, d, J = 15.0 Hz),
   5.26(1H, d, J = 15.0 Hz), 6.79~7.48(13H, m)
EIMS m/e;388(M$^+$), 300(M$^+$–88, 100%)
045*[1]:
NMR(CDCl$_3$) δ(ppm) ;1.94(3H, s) 3.90~4.14(4H, m), 4.61(1H, d, J = 14.7 Hz),
   5.55(1H, d, J = 14.7 Hz), 5.87(1H, s), 6.91~6.99(5H, m) 7.08~7.40(7H, m)
   7.50~7.62(1H, m)
FABMS m/e;390(M$^+$+ 1), 286(M$^+$–103 100%)
048*[1]:
NMR(CDCl$_3$) δ(ppm) ;1.02(3H, t, J = 7.2 Hz), 1.97(3H, s), 2.56~2.72(2H, m),
   5.07 (JH, d, J = 15.6 Hz), 5.35 (1H, d, J = 15.6 Hz), 6.85~7.75 (13H, m)
EIMS m/e;373(M$^+$), 330(M$^+$–43 100%)

TABLE 2-continued

050*[1]:
NMR(CDCl$_3$) δ(ppm) ;0.89(3H, t, J = 7.3 Hz), 1.37~1.55(2H, m), 1.96(3H, s),
2.42~2.51 (2H m), 4.68(1H, d, J = 14.5 Hz), 5.20(1H, d, J = 14.5 Hz),
6.81~7.37(~3H, m)
SIMS m/e;360(M$^+$+ 1, 100%)
051*[1]:
NMR(CDCl$_3$) δ(ppm) ;1.93(3H, s), 4.67(1H, d, J = 14.5 Hz),
5.22(1H, dd, J = 10.8, 1.5 Hz), 5.35(1H, d, J = 14.5 Hz),
5.51 (1H, dd, J = 17.4, 1.5 Hz), 6.80~7.44(14H, m)
EIMS m/e;343(M$^+$), 117(M$^+$−226, 100%)
055*[1]:
NMR(CDCl$_3$) δ(ppm) ;1.92(3H, s), 2.89(6H, s), 4.44(1H, d, J = 14.3 Hz),
5.09(1H, d, J = 14.3 Hz), 6.53~6.60(2H, m), 6.80~7.34(11H, m)
EIMS m/e;360(M$^+$), 134(M$^+$−226, 100%)
064*[1]:
NMR(CDCl$_3$) δ(ppm) ;1.08(3H, t, J = 6.5 Hz), 2.16(2H, q, J = 6.5 Hz), 3.56(3H, s),
4.69(1H, d, J = 14.5 Hz), 5.22(1H, d, J = 14.5 Hz), 6.70~7.40(13H, m)
EIMS m/e;361(M$^+$), 121(M$^+$−240, 100%)
065*[1]:
NMR(CDCl$_3$) δ(ppm) ;1.10(3H, t, J = 7.5 Hz), 2.16(2H, q, J = 7.5 Hz), 3.59(3H, s),
4.69(1H, d, J = 14.4 Hz), 5.19(1H, d, J = 14.4 Hz), 6.70~7.45(12H, m)
EIMS m/e;397(M$^+$+ 2), 395(M$^+$), ~2~(M$^+$−274, 100%)
068*[1]:
NMR(CDCl$_3$) δ(ppm) ;1.05~1.38(9H, m), 2.15(2H, q, J = 7.4 Hz), 4.27~4.88(1H, m),
4.69(1H, d, J = 14.4 Hz), 5.18(1H, d, J = 14.4 Hz), 6.66~7.42(12H, m)
EIMS m/e;425(M$^+$+ 2), 423(M$^+$), ~49(M$^+$−274, 100%)
069*[1]:
NMR(CDCl$_3$) δ(ppm) ;1.10(3H, t, J = 7.5 Hz), 2.16(2H, q, J = 7.5 Hz), 3.54(3H, s),
3.68(3H, s), 4.67(1H, d, J = 14.5 Hz), 5.17(1H, d, J = 14.5 Hz), 6.65~7.43(11H, m)
EIMS m/e;427(M$^+$+ 2),425(M$^+$), 151(M$^+$−274, 100%)
070*[1]:
NMR (CDCl$_3$) δ(ppm) ; 1.09 (3H, t, J = 7.5 Hz), 2.20 (2H, q, J = 7.5 Hz), 3.69 (3H, s)
5.18(1H, d, J = 15.5 Hz), 5.55(1H, d, J = 15.5 Hz), 6.80~7.44(HH, m),
7.59~7.68(1H, m), 7.74~7.83(1H, m)
EIMS m/e;389(M$^+$), 332(M$^+$−57, 100%)
071*[1]:
NMR(CDCl$_3$) δ(ppm);0.86(3H, t, J = 7.4 Hz), 1.55~1.73(2H,m), 2.12(2H, t, J = 7.3 Hz),
3.57(3H, s), 4.67(1H, d, J = 14.6 Hz), 5.23(1H, d, J = 14.6 Hz), 6.71~7.38(13H, m)
EIMS m/e;375(M$^+$), 121(M$^+$−254, 100%)
073*[1]:
NMR(CDCl$_3$) δ(ppm) ;0.83(3H, t, J = 7.3 Hz), 1.17~1.35(2H, m), 1.52~1.69(2H, m),
2.14(2H, t, J = 7.5 Hz), 3.57(3H, s), 4.66(1H, d, J = 14.5 Hz),
5.23(1H, d, J = 14.5 Hz), 6.71~7.38(13H, m)
EIMS m/e;389(M$^+$), 121(M$^+$−268, 100%)
074*[1]:
NMR(CDCl$_3$) δ(ppm) ;0.88(6H, d, J = 6.6 Hz), 2.03(2H, d, J = 6.6 Hz),2.09~2.16(1H, m),
3.58(3H, s), 4.65(1H, d, J = 14.5 Hz), 5.26(1H, d, J = 14.5 Hz), 6.71~7.38(13H, m)
EIMS m/e;389(M$^+$), 121(M$^+$−268, 100%)
075*[1]:
NMR(CDCl$_3$) δ(ppm) ;0.81~0.87(3H, m), 1.12~1.30(4H, m), 1.51~1.69(2H, m)
2.13(2H, t, J = 7.5 Hz), 3.57(3H, s) 4.66(1H, d, J = 14.7 Hz),
5.23(1H, d, J = 14.7 Hz), 6.7I~7.37(13H, m)
EIMS m/e;403(M$^+$), 121(M$^+$−282, 100%)
080*[1]
NMR(CDCl$_3$) δ(ppm) ;3.61(3H, s), 4.66(1H, d, J = 14.1 Hz), 5.40(1H, d, J = 14.1 Hz),
6.72~7.44(13H, m)
EIMS m/e;401 (M$^+$), 121 (M$^+$−280, 100%)
082*[1]:
NMR(CDCl$_3$) δ(ppm) ;2.15(3H, s), 3.58(3H, s), 4.46(1H, d, J = 14.8 Hz),
4.59(1H, d, J = 14.8 Hz), 4.74(1H, d, J = 14.5 Hz), 5.16(1H, d, J = 14.5 Hz),
6.71~7.38(13H, m)
EIMS m/e;405(M$^+$), 121 (M$^+$−284, 100%)
083*[1]:
NMR(CDCl$_3$) δ(ppm) ;3.56(3H, s), 3.64(1H, d, J = 15.9 Hz), 3.76(1H, d, J = 15.9 Hz),
4.78(1H d, J = 14.2 Hz), 5.18(1H, d, J = 14.2 Hz), 6.71~7.40(13H, m)
EIMS m/e;388(M$^+$), 121(M$^+$−267, 100%)
087*[1]:
NMR(CDCl$_3$) δ(ppm) ;3.62(3Hx3/4, s), 3.78(3Hx1/4, s), 4.75(2Hx1/4, s),
4.99(2Hx3/4, s), 6.72~7.40(13H, m), 8.35(1Hx3/4, s), 8.47(1Hx1/4, s)
CIMS m/e;334(M$^+$+ 1), 121(M$^+$−2~2, 100%)
088*[1]:
NMR(CDCl$_3$) δ(ppm) ;1.23(3Hx3/4, t, J = 6.9 Hz), 1.40(3Hx1/4, t, J = 6.9 Hz),
3.84(2Hx3/4, q, J = 6.9 Hz), 3.98(2Hx1/4, q, J = 6.9 Hz), 4.75(2Hx1/4, s),
5.00(2Hx3/4, s), 6.70~7.43(13H m), 8.34(~Hx3/4, s), 8.48(1Hx1/4, s)
CIMS m/e;348(M$^+$+ 1), 135(M$^+$−212, 100%)
098*[1]:
NMR(CDCl$_3$) δ(ppm) ;3.58(3H, s), 3.63(3H, s), 4.82(2H, br s),
6.75~7.42(13H,m)
EIMS m/e;363(M$^+$), 121(M$^+$−242, 100%)

TABLE 2-continued

099*[1]:
NMR(CDCl$_3$) δ(ppm) ;1.06~1.25(3H m), 3.63(3H s), 3.98~4.15(2H, m),
  4.82 (2H, br s), 6.75~7.41 (13H, m)
EIMS m/e;377(M$^+$), 121(M$^+$−256, 100%)
100*[1]:~:
NMR(CDCl$_3$) δ(ppm) ;2.00(3H, s), 2.22(3H, s), 3.58(3H s),
  4.73(1H, d, J = 14.6 Hz), 5.28 (1H, d, J = 14.6 Hz), 6.64(1H, dd, J = 8.2, 1.2 Hz),
  6.65~7.34(10H, m), 7.38(1H, dd, J = 7.5, 1.8 Hz)
EIMS m/e;361(M$^+$), 121(M$^+$−240, 100%)
101*[1]:
NMR(CDCl$_3$) δ(ppm) ;1.95(3H, s), 2.33(3H, s),3.58(3H, s),
  4.71 (1H, d, J = 14.6 Hz), 5.16(1H, d, J = 14.6 Hz), 6.70~7.30(11H, m),
  7.35 (1H dd, J = 7.5, 1.5 Hz)
EIMS m/e;361 (M$^+$), 121 (M$^+$−240, 100%)
103*[1]:
NMR(CDCl$_3$) δ(ppm) ;2.02(3H s), 3.61 (3H, s), 3.75(3H, s),
  4.74(1H, d, J = 14.7 Hz), 5.26(1H, d, 14.7 Hz), 6.57(1H, dd, J = 8.3, 1.2 Hz),
  6.76(1H, d, J = 8.3 Hz), 6.78~7.26(9H, m), 7.39(1H, dd, J = 7.5, 1.8 Hz)
EIMS m/e;377(M$^+$), 121(M$^+$−256, 100%)
104*[1]:
NMR(CDCl$_3$) δ(ppm) ;1.94(3H, s), 3.57(3H, s), 3.79(3H, s)
  4.69(1H, d, J = 14.6 Hz), 5.17(1H, d, J = 14.6 Hz), 6.43~6.55(2H, m),
  6.62~7.05(6H, m), 7.10~7.29(3H, m), 7.35(1H, dd, J = 7.5, 1.8 Hz)
EIMS m/e;377(M$^+$), 121(M$^+$−256, 100%)
105
NMR(CDCl$_3$) δ(ppm) ;1.96(3H, s), 3.58(3H, s), 3.81 (3H, s),
  4.77(1H, d, J = 14.6 Hz), 5.16(1H, d, J = 14.6 Hz), 6.70~6.74(2H, m),
  6.79~7.25 (9H, m), 7.36 (1H, dd, J = 7.5, 1.8 Hz)
EIMS m/e;377(M$^+$), 121(M$^+$−256, 100%)
109*[1]:
NMR(CDCl$_3$) δ(ppm) ;1.94(3H, s), 3.56(3H, s), 4.75(1H, d, J = 14.6 Hz),
  5.12(1H, d, J = 14.6 Hz), 6.67~7.25(11H, m), 7.34(1H, dd, J = 7.5, 1.8 Hz)
EIMS m/e;365(M$^+$), 121(M$^+$−244, 100%)
118*[1]:
NMR(CDCl$_3$) δ(ppm) ;1.96(3H, s) 3.52(3H, s), 4.96(1H, d, J = 14.5 Hz),
  5.02(1H, d, J = 14.5 Hz), 6.50~7.42(12H, m)
FABMS m/e;366(M$^+$+ 1), 121 (M$^+$−244, 100%)
127*[1]:
NMR(CDCl$_3$) δ(ppm) ;1.97(3H, s), 3.64(3H s), 4.70(1H, d, J = 14.5 Hz),
  5.16(1H, d, J = 14.5 Hz), 6.47~6.60(2H, m), 6.73~7.38(15H, m)
FABMS m/e;440(M$^+$+ 1), 121(M$^+$−318, 100%)
150*[1]:
NMR(CDCl$_3$) δ(ppm) ;2.00(3H, s), 2.25(6H, s), 3.43(1H, d, J = 115 Hz),
  3.52(1H, d, J = 11.5 Hz), 3.59(3H, s), 4.68(1H, d, J = 14.7 Hz),
  5.30(1H, d, J = 14.7 Hz), 6.64~7.56(12H, m),
FABMS m/e;405(M$^+$+ 1, 100%)
151*[1]:
NMR(CDCl$_3$) δ(ppm) ;1.95(3H, s), 2.24(6H, s), 3.40(2H, s), 3.59(3H, s)
  4.68(1H, d, J = 14.6 Hz), 5.19(1H, d, J = 14.6 Hz), 6.70~7.40(12H, m)
FABMS m/e;405(M$^+$+ 1, 100%)
152*[1]:
NMR(CDCl$_3$) δ(ppm) ;1.95(3H, s), 2.25(6H, s), 3.40(2H, s), 3.59(3H, s)
  4.68(1H, d, J = 14.5 Hz), 5.19(1H, d, J = 14.5 Hz), 6.68~7.40(12H, m)
EIMS m/e;404(M$^+$), 317(M$^+$−87, 160%)
160*[1]:
NMR(CDCl$_3$) δ(ppm) ;1.95(3H, s), 3.53(3H, s), 3.65(3H, s), 4.77(1H d, J = 14.7 Hz),
  5.04(1H, d, J = 14.7 Hz), 6.60~7.63(11H, m)
EIMS m/e;420(M$^+$), 151(M$^+$−269, 100%)
167*[1]:
NMR(CDCl$_3$) δ(ppm) ;1.12(3H, d, J = 6.2 Hz), 1.17(3H d, J = 6.2 Hz), 1.92(3H, s)
  4.37(1H, sept, J = 6.2 Hz), 4.73(1H, d, J = ~4.3 Hz), 5.07(1H, d, J = 14.3 Hz),
  6.52 (1H, ddd, J = 9.7, 2.4, 2.4 Hz), 6.62~7.39 (10H, m)
FABMS m/e;428(M$^+$+ 1), 149(M$^+$−278, 100%)
168*[1]:
NMR(CDCl$_3$) δ(ppm) ;1.11(3H, d, J = 6.0 Hz), 1.14(3H, d, J = 6.0 Hz), 1.93(3H, s)
  2.25(3H, s);4.35(1H, sept, J = 6.0 Hz), 4.68(1H, d, J = 14.5 Hz),
  5.03(1H, d, J = 14.5 Hz), 6.42~6.53(1H, m), 6.60~7.40(10H, n)
FABMS n/e;408(M$^+$+ 1), 149(M$^+$−258, 100%)
169*[1]:
NMR(CDCl$_3$) δ(ppm) ;1.11(3H, d, J = 6.0 Hz), 1.14(3H, d, J = 6.0 Hz), 1.94(3H, s)
  2.22(3H, s), 4.36(1H, sept, J = 6.0 Hz), 4.73(1H, d, J = 14.6 Hz),
  5.04(1H, d, J = 14.6 Hz), 6.65~7.20(I0H, m), 7.36(1H, dd, J = 7.5, 1.8 Hz)
FABMS n/e;408(M$^+$+ 1), 149(M$^+$−258, 100%)
170*[1]:
NMR(CDCl$_3$) δ(ppm) ; 1.11 (3H, d, J = 6.0 Hz), 1.16 (3H, d, J = 6.0 Hz), 1.95 (3H, s)
  2.20(3H, s), 2.~32(3H, s), 4.37(1H, sept, J = 6.0 Hz), 4.67(1H, d, J = 14.7 Hz),
  5.10(1H, d, J = 14.7 Hz), 6.68~7.20(10H, m), 7.38(1H, dd, J = 7.5, 1.5 Hz)
FABMS n/e;404(M$^+$+ 1), 149(M$^+$−254, 100%)

TABLE 2-continued

171*[1]:
NMR(CDCl$_3$) δ(ppm) ;1.95(3H, s), 2.24(3H, s), 3.53(3H, s), 3.67(3H, s)
  4.72(1H, d, J = 14.7 Hz), 5.04(1H, d, J = 14.7 Hz), 6.62~7.06(10H, m)
FABMS m/e;410(M$^+$+ 1), 151(M$^+$−258, 100%)
177*[1]:
NMR(CDCl$_3$) δ(ppm) ;1.92(3H, s), 2.74~3.12(2H, m), 3.58~3.77(1H, m),
  4.05~4.21 (1H, m), 4.85~5.12(2H, m), 6.93(1H, d, J = 6.9 Hz),
  6.97~7.53(10H, m), 7.79(1H, dd, J = 8.8, 2.4 Hz)
FABMS m/e;445(M$^+$+ 1, 100%)
178*[1]:
NMR(CDCl$_3$) δ(ppm) ;1.93(3H, s), 2.78~3.13(2H, m), 3.60~3.92(1H, m),
  3.73(3H, s), 4.04~4.23(1H, m), 4.72~5.02(2H, m), 6.77~7.50(11H, m),
  7.75 (1H, dd, J = 8.8, 2.4 Hz)
FABMS m/e;441 (M$^+$+ 1, 100%)
179*[1]:
NMR(CDCl$_3$) δ(ppm) ;1.02~1.23(9H, m), 2.12(2H, q, J = 7.3 Hz),
  4.37(1H, sept, J = 6.0 Hz), 4.~70(1H, d, J = 14.3 Hz), 5.11 (1H, d, J = 14.3 Hz),
  6.53(1H, ddd, J = 9.7, 2.3, 2.3 Hz), 6.63~7.39(10H, m)
FABMS m/e;442(M$^+$+ 1), 154(M$^+$−287, 100%)
180*[1]:
NMR(CDCl$_3$) δ(ppm);1.00~1.22(9H, m), 2.14(2H, t, J = 7.5 Hz),
  4.38(1H, sept, J = 6.0 Hz), 4.75(1H, d, J = 14.3 Hz), 5.12(1H, d, J = 14.3 Hz),
  6.63~7.23(10H, m), 7.36(1H, dd, J = 7.5, 1.5 Hz),
FABMS m/e;442(M$^+$+ 1), 154(M$^+$−287, 100%)
183*[1]:
NMR(CDCl$_3$) δ(ppm);1.10(3H, t, J = 7.4 Hz), 2.13(2H, q, J = 7.4 Hz), 3.53(3H, s),
  3.68(3H, s), 4.68(1H, d, J = 14.4 Hz), 5.H (1H, d, J = 14.4 Hz),
  6.51~7.06(9H, n), 7.22~7.40(1H, m)
FABMS m/e;444(M$^+$+ 1), 154(M$^+$−289, 100%)
184*[1]:
NMR(CDCl$_3$) δ(ppm);1.11(3H, t, J = 7.5 Hz), 2.15(2H, q, J = 7.5 Hz), 3.53(3H, s),
  3.68(3H, s), 4.71(1H, d, J = 14.5 Hz), 5.13(1H, d, J = 14.5 Hz), 6.63~7.14(10H, m),
FABMS m/e;444(M$^+$+ 1), 151(M$^+$−292, 100%)
186*[1]:
NMR(CDCl$_3$) δ(ppm) ;1.12(3H, t, J = 7.5 Hz), 2.17(3H, q, J = 7.5 Hz), 3.54(3H, s),
  3.69(3H, s), 3.83(3H, s), 4.72(1H, d, J = 14.5 Hz), 5.16(1H, d, J = 14.5 Hz),
  6.65~7.00(10H, m)
FABMS m/e;456(M$^+$+ 1), 154(M$^+$−301,~100%)
187*[1]:
NMR(CDCl$_3$) δ(ppm) ;1.00~1.24(9H, m), 2.13(2H, q, J = 7.5 Hz), 2.24(3H, s),
  4.35(1H, sept, J = 5.9 Hz), 4.65(1H, d, J = 14.5 Hz), 5.07(1H, d, J = 14.7 Hz),
  6.48(1H, ddd, J = 10.2, 2.4, 2.4 Hz), 6.58~6.90(6H, m), 6.95~7.40(4H, m)
FABMS m/e;422(M$^+$+ 1), 149(M$^+$−272, 100%)
189*[1]: :
NMR(CDCl$_3$) δ(ppm) ; 1.02~1.25 (9H, m), 2.17(2H, q, J = 7.5 Hz), 2.19(3H, s),
  3.80(3H, s), 4.36(1H, sept, J = 6.0 Hz), 4.71(1H, d, J = 14.6 Hz),
  5.12(1H d, J = 14.6 Hz), 6.64(1H, d, J = 8.4 Hz), 6.62~6.99(8H, m),
  7.07~7.20 (~H, m), 7.41 (1H, dd, J = 7.6, 1.7 Hz)
FABMS m/e;434(M$^+$+ 1), 107(M$^+$−326, 100%)
193*[1]:
NMR(CDCl$_3$) δ(ppm) ;1.18(6H, d, J = 5.9Hz), 2.75(3H, d, J = 4.6 Hz),
  4.44(1H, sept, J = 5.9 Hz), 4.46(1H, br s), 4.80(2H, s),
  6.55~7.40(11H, m)
FABMS m/e;443(M$^+$+ 1), 149(M$^+$−293, 100%)
194*[1]:
NMR(CDCl$_3$) δ(ppm) ;1.18(6H, d, J = 6.l Hz), 2.35(3H, s), 2.77(3H, d, J = 4.8 Hz),
  4.42(1H, sept, J = 6.1 Hz), 4.43(1H, br s), 4.86(2H, s), 6.72~7.22(10H, m),
  7.42 (1H, dd, J = 7.5, 1.8 Hz)
FABMS m/e;439(M$^+$+ 1), 154(M$^+$−284, 100%)
195*[1]:
NMR(CDCl$_3$) δ(ppm) ;1.18(6H, d, J = 6.2 Hz), 2.79(3H, d, J = 4.6 Hz), 3.82(3H, s),
  4.43(1H, sept, J = 6.2 Hz), 4.44(1H, br s), 4.87(2H, s), 6.72(1H, d, J = 2.2 Hz),
  6.73~6.96(7H, m), 7.00(1H, d, J = 8.4 Hz), 7.12~7.23(1H, m),
  7.42(1H, dd, J = 7.5, 1.8 Hz)
FABMS m/e;455(M$^+$+ 1), 107(M$^+$−347, 100%)
197*[1]:
NMR(CDCl$_3$) δ(ppm) ;1.16(6H, d, J = 5.9 Hz), 2.22(3H, s), 2.76(3H, d, J = 4.6 Hz),
  3.81 (3H, s), 4.41 (1H, sept, J = 5.9 Hz), 4.43(1H, br s), 4.77~4.90(2H, m),
  6.63~7.22(10H, m), 7.44~7.53(1H, m)
FABMS m/e;435(M$^+$+ 1), 107(M$^+$−327, 100%)

*[1]: Compound Number (See Table 1)

Experiment MDR Receptor Binding Assay

Crude mitochondria fractions prepared from rat cerebral cortex were used as a receptor sample, and [$^3$H]PK11195 was used as a [$^3$H]-labeled ligand.

A binding assay using the [$^3$H]-labeled ligand was carried out according to the following method as described in Journal of Pharmacology and Experimental Therapeutics, 262, 971(1992).

Preparation of Receptor Sample: Rat cerebral cortex was homogenized using a Teflon-coated homogenizer in a 10 mM HEPES buffer (pH 7.4) containing 0.32 M sucrose in ten volumes of the wet weight. The homogenate was centrifuged at 900×g for 10 minutes, and the resulting supernatant was centrifuged at 9,000×g for 10 minutes. The precipitate was suspended in a HEPES buffer to give a protein concentration of 1 mg/ml, and centrifuged at 12,000×g for 10 minutes. The resulting precipitate was suspended in a 50 mM HEPES buffer (pH 7.4) to give a crude mitochondria fraction.

MDR Binding Assay: Mitochondria sample (1.0 mg protein/ml), [$^3$H]PK11195 (2 nM) and the test drug were reacted at 4° C. for 90 minutes. After completion of the reaction, the reaction mixture was filtered with suction through a glass filter (GF/B) treated with 0.3% polyethyleneimine, and the radioactivity on the filter was measured by a liquid scintillation spectrometer.

The binding at the reaction in the presence of 10 μM PK11195 was defined as non-specific binding of [$^3$H] PK11195, and the difference between total binding and non-specific binding was defined as specific binding. A fixed concentration of [$^3$H]PK11195 (2 nM) was reacted with varied concentrations of the test drug under the abovementioned conditions to give an inhibition curve, and the concentration ($IC_{50}$) of the test drug to exhibit 50% inhibition of [$^3$H]PK11195 binding was measured by the inhibition curve, and results are shown in Table 3.

disorders, recognition and leaning disability or schizophrenia, dyskinesia accompanied by muscle rigidity, feeding disorders, circulation disorders, drug dependence, cancer, lipid metabolism abnormality, cerebral infarction, aids, alzheimer's disease or huntington chorea.

What is claimed is:

1. An aryloxyaniline derivative represented by the formula:

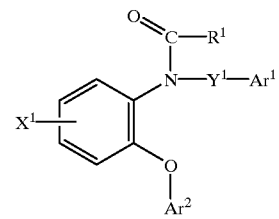

wherein $Ar^1$ and $Ar^2$ are the same or different, and are each a substituted or unsubstituted phenyl group or a naphthyl group, $R^1$ is a hydrogen atom, a substituted or unsubstituted alkyl group having 1 to 10 carbon atoms, an alkoxy group having 1 to 10 carbon atoms, a substituted or unsubstituted phenyl group or a group of the formula:

—$NR^2(R^3)$ (wherein $R^2$ and $R^3$ are the same or different, and are each a hydrogen atom or an alkyl group having 1 to 10 carbon atoms), $X^1$ is a hydrogen atom, an alkyl group having 1 to 5 carbon atoms, an alkoxy group having 1 to 5 carbon atoms, a phenoxy group, a halogen atom, a trifluoromethyl group or a carbamoyl group, $Y^1$ is a branched or unbranched alkylene group having 1 to 6 carbon atoms or a single bond; or a pharmaceutically acceptable salt thereof, and the substituted phenyl group is a phenyl group substituted with one to three members selected from the group consisting of an alkyl group having 1 to 10 carbon atoms, an alkyl group

TABLE 3

| Comp. No. | MDR $IC_{50}$ (nM) | Comp. No. | MDR $IC_{50}$ (nM) | Comp. No. | MDR $IC_{50}$ (nM) | Comp. No. | MDR $IC_{50}$ (nM) |
|---|---|---|---|---|---|---|---|
| 001 | 1.38 | 027 | 3.20 | 066 | 0.925 | 098 | 0.498 |
| 002 | 0.658 | 028 | 3.20 | 067 | 1.08 | 099 | 0.870 |
| 003 | 0.123 | 029 | 0.486 | 071 | 1.26 | 100 | 0.112 |
| 004 | 0.791 | 030 | 1.96 | 072 | 3.51 | 101 | 0.285 |
| 005 | 0.118 | 031 | 1.23 | 073 | 1.52 | 102 | 6.123 |
| 006 | 0.677 | 032 | 6.73 | 075 | 1.83 | 103 | 0.722 |
| 007 | 0.0977 | 033 | 3.51 | 076 | 0.955 | 104 | 0.343 |
| 008 | 0.870 | 034 | 0.179 | 077 | 5.59 | 105 | 0.163 |
| 009 | 0.112 | 040 | 0.0643 | 079 | 4.64 | 108 | 0.413 |
| 010 | 0.149 | 046 | 0.376 | 080 | 4.64 | 109 | 0.285 |
| 011 | 0.163 | 047 | 0..265 | 081 | 0.343 | 110 | 8.90 |
| 012 | 0.453 | 049 | 4.23 | 082 | 8.90 | 112 | 0.376 |
| 013 | 9.77 | 050 | 0.215 | 085 | 3.85 | 116 | 0.343 |
| 014 | 2.21 | 051 | 0.196 | 087 | 0.572 | 117 | 0.792 |
| 015 | 0.285 | 052 | 4.64 | 088 | 0.163 | 118 | 0.498 |
| 016 | 0.722 | 054 | 1.26 | 089 | 3.51 | 120 | 0.196 |
| 017 | 0.0850 | 055 | 1.83 | 090 | 4.64 | 121 | 2.01 |
| 019 | 0.196 | 056 | 2.92 | 091 | 1.83 | 123 | 0.870 |
| 021 | 0.310 | 060 | 0.955 | 092 | 0.722 | 124 | 0.343 |
| 022 | 0.179 | 061 | 0.498 | 093 | 0.870 | 125 | 2.21 |
| 023 | 0.424 | 062 | 1.05 | 094 | 0.925 | 126 | 8.11 |
| 025 | 0.260 | 064 | 0.0933 | 095 | 3.77 | 127 | 3.51 |

INDUSTRIAL APPLICABILITY

The present invention has provided drugs having a high affinity for MDR, and therefore they are useful as therapeutic or preventive drugs of central diseases such as anxiety, related diseases thereto, depression, epilepsy, sleeping having 1 to 10 carbon atoms substituted with halogen atoms; hydroxyl groups; carboxyl groups or alkoxycarbonyl groups, an alkenyl group having 2 to 10 carbon atoms, an alkoxy group having 1 to 10 carbon atoms, an alkylthio group having 1 to 10 carbon atoms, a group of the formula: —O—Z—R$^4$ (wherein Z is a branched or unbranched alkylene group having 1 to 10 carbon atoms, and R$^4$ is an amino group, an amino group substituted with one or two of an alkyl group having 1 to 7 carbon atoms, a cyclic amino group having 2 to 7 carbon atoms, a hydroxyl group, a carboxyl group or an alkoxycarbonyl group), an alkanoyl group having 2 to 10 carbon atoms or a ketal form thereof, a formyl group or an acetal form thereof, a carboxyl group, an alkoxycarbonyl group having 2 to 10 carbon atoms, a carbamoyl group, a carbamoyl group substituted with one or two of an alkyl group having 1 to 10 carbon atoms on the nitrogen atom, an aminosulfonyl group, an aminosulfonyl group substituted with one or two of an alkyl group having 1 to 10 carbon atoms on the nitrogen atom, a halogen atom and a nitro group.

2. A medicine comprising the aryloxyaniline derivative or the pharmaceutically acceptable salt thereof according to claim 1.

3. A ligand for MDR comprising the aryloxyaniline derivative or the pharmaceutically acceptable salt thereof according to claim 1 as an active ingredient.

* * * * *

UNITED STATES PATENT AND TRADEMARK OFFICE
CERTIFICATE OF CORRECTION

PATENT NO. : 6,333,358 B1
DATED : December 25, 2001
INVENTOR(S) : Nakazato et al.

It is certified that error appears in the above-identified patent and that said Letters Patent is hereby corrected as shown below:

Column 2,
Line 33, "$y^1$" should read -- $Y^1$ --.

Column 4,
Line 45, "allcylene" should read -- alkylene --.

Column 7,
Line 14, "allcoxycarbonyl" should read -- alkoxycarbonyl --.

Column 27,
Line 41, "038*hu 1:" should read -- $038^{*1}$: --.

Column 31,
Line 5, "$100^{*1}$:~:" should read -- $100^{*1}$: --.

Column 33,
Line 17, "4.~70" should read -- 4.70 --; and
Line 44, "$189^{*1}$::" should read -- $189^{*1}$: --.

Column 35,
Table 3, line 5, last column, under the heading "MDR $IC_{50}$ (nM)", "6.123" should read -- 0.123 --; and
Table 3, line 11, fourth column, under the heading "MDR $IC_{50}$ (nM)", "0..265" should read -- 0.265 --.

Signed and Sealed this

Third Day of September, 2002

*Attest:*

JAMES E. ROGAN
*Attesting Officer*     *Director of the United States Patent and Trademark Office*